United States Patent
Herlihy et al.

(10) Patent No.: US 7,671,081 B2
(45) Date of Patent: Mar. 2, 2010

(54) MULTIFUNCTIONAL CATIONIC PHOTOINITIATORS, THEIR PREPARATION AND USE

(75) Inventors: Shaun Lawrence Herlihy, Kent (GB); Brian Rowatt, Kent (GB); Robert Stephen Davidson, Leicester (GB)

(73) Assignee: Sun Chemical Corporation, Parsippany, NJ (US)

( * ) Notice: Subject to any disclaimer, the term of this patent is extended or adjusted under 35 U.S.C. 154(b) by 223 days.

(21) Appl. No.: 11/934,387

(22) Filed: Nov. 2, 2007

(65) Prior Publication Data
US 2009/0023829 A1  Jan. 22, 2009

Related U.S. Application Data

(62) Division of application No. 10/538,243, filed as application No. PCT/US03/39098 on Dec. 10, 2003, now Pat. No. 7,294,723.

(30) Foreign Application Priority Data
Dec. 10, 2002  (GB) .................................. 0229081.5

(51) Int. Cl.
*A61K 31/381* (2006.01)
*C07D 333/46* (2006.01)
*C07D 333/76* (2006.01)

(52) U.S. Cl. ........................................ 514/443; 549/48

(58) Field of Classification Search ................ 514/443; 549/48
See application file for complete search history.

(56) References Cited

U.S. PATENT DOCUMENTS

| | | | |
|---|---|---|---|
| 4,161,478 A | 7/1979 | Crivello | |
| 5,113,876 A | 5/1992 | Herman | |
| 5,731,364 A | 3/1998 | Sinta et al. | |
| 5,905,164 A | 5/1999 | Anderson et al. | |
| 7,101,998 B2 | 9/2006 | Herlihy et al. | |
| 7,166,647 B2 | 1/2007 | Herlihy et al. | |
| 7,176,317 B2 | 2/2007 | Banning et al. | |

FOREIGN PATENT DOCUMENTS

| | | |
|---|---|---|
| EP | 0869393 | 10/1998 |
| WO | 03/007258 | 9/2003 |
| WO | 03/072567 | 9/2003 |
| WO | 03/098347 | 11/2003 |

*Primary Examiner*—Taofiq A Solola
(74) *Attorney, Agent, or Firm*—Kramer Levin Naftalis & Frankel LLP

(57) ABSTRACT

Compounds of formula (I):

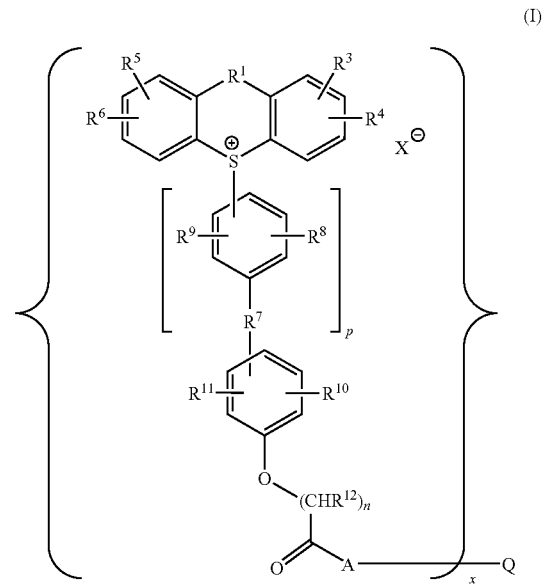

wherein the substituents are as defined herein.

31 Claims, No Drawings

MULTIFUNCTIONAL CATIONIC PHOTOINITIATORS, THEIR PREPARATION AND USE

RELATED APPLICATIONS

This application is a divisional of U.S. application Ser. No. 10/538,243, filed May 15, 2006, now pending, which is a U.S. National Stage application of PCT/US03/39098, filed Dec. 10, 2003, which claims priority of the Great Britain application no. 0229081.5, filed Dec. 10, 2002, the contents of each are hereby incorporated by reference in their entirety.

The present invention relates to a series of novel sulphonium salts which are useful as multifunctional cationic photoinitiators, especially for use in surface coating applications, such as printing inks and varnishes, and which are intended to be cured by polymerisation initiated by radiation.

Photocurable compositions are cured by exposure to radiation, usually ultraviolet radiation, and include for example, lacquers which may be applied to wood, metal or similar substrates by suitable techniques such as roll coating or curtain coating. They may also be formulated as inks, for example to be applied by techniques such as letterpress, offset lithography, rotogravure printing, silk screen printing, inkjet or flexographic printing. Printing, depending on the particular printing technique, is applicable to a wide range of substrates which include paper, board, glass, plastics materials or metals. Other application areas will include adhesives, powder coatings, circuit boards and microelectronic products, stereolithography, composites, optical fibres and liquid crystals.

Initiation of polymerisation in a monomer, oligomer or prepolymer may be effected in a number of ways. One such way is by irradiation, for example with ultraviolet radiation, in which case it is normally necessary mat the polymerisable composition should contain an initiator, commonly referred to as a "photoinitiator", or alternatively by an electron beam. There are two main types of curing chemistry which can be used in this process; free radical and cationic. Although cationic curing has many advantages, its disadvantages, particularly with regard to the photoinitiators used, leads it to be used only in a minority of applications. Most frequently used cationic initiators are either organic iodonium or sulphonium salts.

Briefly, the mechanism by which a sulphonium cationic initiator acts when irradiated is that it forms an excited state which then breaks down to release a radical cation. This radical cation reacts with the solvent, or another hydrogen atom donor, generating a protonic acid. The active species is the protonic acid. However, amongst the breakdown products of sulphonium salts are aromatic sulphides, such as diphenyl sulphide, which are malodorous and can be a health hazard, and lower aromatic hydrocarbons, such as benzene, which are potentially carcinogenic. Many of the commonly used iodonium salts break down to give volatile species such as benzene, toluene or isobutyl benzene. This places sever restrictions upon the applications for which such cationic photoinitiators can be used. For example, they cannot be used in printing inks on packaging intended for food or is likely to come into contact with food, and, in some cases, cannot be used at all where the packaging is to be handled by the consumer. Indeed, as the industry becomes ever more conscious of health matters, it is increasingly difficult to use such compounds at all and there is, therefore, an urgent need to find compounds suitable for use as photoinitiators and whose breakdown products are generally regarded as safe.

However, this, although important, is not the only constraint upon the choice of compound to be used as a cationic photoinitiator. Even without consideration of the health issues, the cleavage products of the known cationic photoinitiators are malodorous, and it is highly desirable that unpleasant odours should be minimised. This leads to a desire that the cleavage products should be relatively non-volatile and non-odorous. The cationic photoinitiators must, of course, also be sufficiently stable, both as isolated compounds and when in the uncured coating formulation. They must also be soluble in or miscible with other components of the uncured coating formulation. Finally, they should be able to absorb radiation over a suitable and sufficiently wide range of wavelengths, ideally without the use of a sensitiser.

What is more, the nature of the cationic photoinitiator can have a major impact on the properties of the cured coating. The cationic photoinitiator should produce a coating which is fully cured, hard and resistant to common solvents and abuse.

Finally, there are a number of practical problems associated with the manufacture of the compounds used as cationic photoinitiators, including the necessity that they should be relatively easy and inexpensive to manufacture.

Thus, it would be desirable to provide a cationic photoinitiator which does not generate malodorous or toxic by-products upon radiation cure, particularly diphenyl sulphide and benzene, and so which may be used for printing packaging which may come into contact with food. Moreover, it is a common desideratum in this field that the photoinitiator should possess the following properties: good solubility, good cure performance, good adhesion to substrates and reasonable cost.

Not surprisingly, complying with all of these, often conflicting, requirements is not easy, and we are not aware of any completely satisfactory commercial solution available until now.

However, we have now discovered a series of new derivatives of thioxanthone and similar fused ring compounds, whose breakdown products include examples mat are widely used as free radical photoinitiators and whose safety is not in question. Moreover, many of these compounds have the advantages of good solubility in the coating composition combined with excellent cure.

Thus, the present invention provides photoinitiator compounds of formula (I):

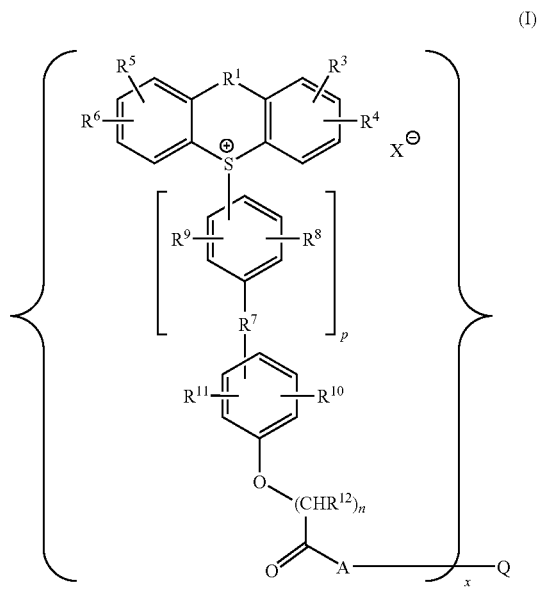

where:

$R^1$ represents a direct bond, an oxygen atom, a group >CH$_2$, a sulphur atom, a group >C=O, a group —(CH$_2$)$_2$— or a group of formula —N—R$^a$, where R$^a$ represents a hydrogen atom or a C$_1$-C$_{12}$ alkyl group;

$R^3$, $R^4$, $R^5$ and $R^6$ are independently selected from hydrogen atoms and substituents α, defined below;

$R^8$, $R^9$, $R^{10}$ and $R^{11}$ are independently selected from hydrogen atoms, hydroxy groups, C$_1$-C$_4$ alkyl groups, and phenyl groups which are unsubstituted or substituted by at least one substituent selected from the group consisting of C$_1$-C$_4$ alkyl groups and C$_1$-C$_4$ alkoxy groups;

or $R^9$ and $R^{11}$ are joined to form a fused ring system with the benzene rings to which they are attached;

$R^7$ represents a direct bond, an oxygen atom or —CH$_2$— group;

p is 0 or 1;

said substituents α are: a C$_1$-C$_{20}$ alkyl group, a C$_1$-C$_{20}$ alkoxy group, a C$_2$-C$_{20}$ alkenyl group, a halogen atom, a nitrile group, a hydroxyl group, a C$_6$-C$_{10}$ aryl group, a C$_7$-C$_{13}$ aralkyl group, a C$_6$-C$_{10}$ aryloxy group, a C$_7$-C$_{13}$ aralkyloxy group, a C$_9$-C$_{12}$ arylalkenyl group, a C$_3$-C$_8$ cycloalkyl group, a carboxy group, a C$_2$-C$_7$ carboxyalkoxy group, a C$_2$-C$_7$ alkoxycarbonyl group, a C$_7$-C$_{13}$ aryloxycarbonyl group, a C$_2$-C$_7$ alkylcarbonyloxy group, a C$_1$-C$_6$ alkanesulphonyl group, a C$_6$-C$_{10}$ arenesulphonyl group, a C$_1$-C$_6$ alkanoyl group or a C$_7$-C$_{11}$ arylcarbonyl group;

n is a number from 1 to 12;

$R^{12}$ represents a hydrogen atom, a methyl group or an ethyl group, and, when n is greater than 1, the groups or atoms represented by $R^{12}$ may be the same as or different from each other;

A represents a group of formula —[O(CHR$^{13}$CHR$^{14}$)$_a$]$_y$—, —[O(CH$_2$)$_b$CO]$_y$—, or —[O(CH$_2$)$_b$CO]$_{(y-1)}$—[O(CHR$^{13}$CHR$^{14}$)$_a$]—, where:

one of $R^{13}$ and $R^{14}$ represents a hydrogen atom and the other represents a hydrogen atom, a methyl group or an ethyl group;

a is a number from 1 to 2;

b is a number from 4 to 5;

Q is a residue of a polyhydroxy compound having from 2 to 6 hydroxy groups;

x is a number greater than 1 but no greater than the number of available hydroxyl groups in Q;

y is a number from 1 to 10; and

X$^-$ represents an anion;

and esters thereof.

These compounds are useful as photoinitiators for use in energy, e.g. UV, curable coating compositions, including varnishes, lacquers and printing inks, most especially printing inks.

The compounds of the present invention may, as described above, be used as cationic photoinitiators for radiation-curable coating compositions. Thus, the present invention also provides an energy-curable composition comprising: (a) a polymerisable monomer, prepolymer or oligomer, especially a material which undergoes acid-catalysed ring opening polymerisation, e.g. an epoxide (oxirane) or oxetane, or an ethylenically unsaturated material, such as vinyl or propenyl ethers and (b) a cationic photoinitiator which is a compound of formula (I), as defined above, or an ester thereof.

The invention still further provides a process for preparing a cured polymeric composition by exposing a composition of the present invention to curing energy, preferably ultraviolet radiation.

Preferably, when x is a number greater than 1 but no greater than 2, y is a number from 1 to 10; or when x is a number greater than 2, y is a number from 3 to 10.

Where $R^1$ represents a group of formula —N—R$^a$, R$^a$ represents a hydrogen atom or an alkyl group having from 1 to 12 carbon atoms, more preferably from 1 to 6 carbon atoms, and most preferably from 1 to 4 carbon atoms, for example any of the alkyl groups having this number of carbon atoms and described below in relation to R$^3$ etc., preferably a hydrogen atom or a methyl or ethyl group.

However, we most prefer those compounds in which $R^1$ represents a group >C=O, a sulphur atom or a direct bond, and especially those in which $R^1$ represents a group >C=O.

More preferred are those compounds of formula (I) in which the residue of formula (IV):

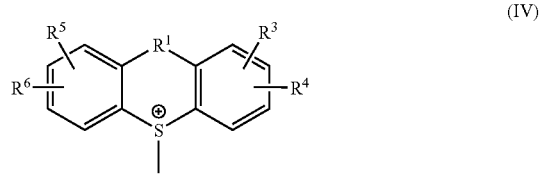

is a residue of substituted or unsubstituted thianthrene, dibenzothiophene, thioxanthone, thioxanthene, phenoxathiin or phenothiazine, especially those in which said residue is a substituted or unsubstituted thioxanthone.

We also particularly prefer compounds in which p is 0.

Where $R^3$, $R^4$, $R^5$ or represents an alkyl group having from 1 to 20, preferably from 1 to 10, more preferably from 1 to 6 and most preferably from 1 to 3, carbon atoms, this may be a straight or branched chain group, and examples of such groups include the methyl, ethyl, propyl, isopropyl, butyl, isobutyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl, decyl, dodecyl, tridecyl, pentadecyl, octadecyl, nonadecyl and icosyl groups, but preferably the methyl, ethyl, propyl, isopropyl and t-butyl groups, and most preferably the ethyl or isopropyl group.

Where $R^3$, $R^4$, $R^5$ or $R^6$ represents an alkoxy group having from 1 to 20, preferably from 1 to 10, more preferably from 1 to 6 and most preferably from 1 to 3, carbon atoms, this may be a straight or branched chain group, and examples of such groups include the methoxy, ethoxy, propoxy, isopropoxy, butoxy, isobutoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy, isohexyloxy, heptyloxy, 2-ethylhexyloxy, octyloxy, nonyloxy, decyloxy, dodecyloxy, tridecyloxy, pentadecyloxy, octadecyloxy, nonadecyloxy and icosyloxy groups, but preferably the methoxy, ethoxy, t-butoxy and 2-ethylhexyloxy groups, and most preferably the 2-ethylhexyloxy group.

Where $R^3$, $R^4$, $R^5$ or $R^6$ represents an alkenyl group having from 2 to 20, preferably from 2 to 10, more preferably from 2 to 6 and most preferably from 2 to 4, carbon atoms, this may be a straight or branched chain group, and examples of such groups include the vinyl, 1-propenyl, allyl, isopropenyl, methallyl, butenyl, pentenyl, hexenyl, heptenyl, octenyl, nonenyl, decenyl, dodecenyl, tridecenyl, pentadecenyl, octadecenyl, nonadecenyl and icosenyl groups, but preferably the allyl, methallyl and butenyl groups, and most preferably the allyl group.

Where $R^3$, $R^4$, $R^5$ or $R^6$ represents a halogen atom, this may be, for example, a fluorine, chlorine, bromine or iodine atom, preferably a chlorine atom.

Where $R^3$, $R^4$, $R^5$ or $R^6$ represents an aryl group, this has from 6 to 10 carbon atoms in one or more aromatic carbocyclic rings (which, if there are more than one, may be fused together). Such a group may be substituted or unsubstituted, and, if substituted, the substituent(s) is preferably an alkyl or alkoxy group (as defined above), or an alkoxycarbonyl group (as defined below). Preferred aryl groups are the phenyl and naphthyl (1- or 2-) groups, the phenyl group being most preferred.

Where $R^3$, $R^4$, $R^5$ or $R^6$ represents an aryloxy group, this may be any of the aryl groups above bonded to an oxygen atom, and examples include the phenoxy and naphthyloxy groups.

Where $R^3$, $R^4$, $R^5$ or $R^6$ represents an aralkyl group, this is an alkyl group having from 1 to 4 carbon atoms which is substituted by one or two aryl groups as defined and exemplified above. Examples of such aralkyl groups include the benzyl, α-phenylethyl, β-phenylethyl, 3-phenylpropyl, 4-phenylbutyl, diphenylmethyl, 1-naphthylmethyl and 2-naphthylmethyl groups, of which the benzyl group is preferred.

Where $R^3$, $R^4$, $R^5$ or $R^6$ represents an aralkyloxy group, this may be any of the aralkyl groups above bonded to an oxygen atom, and examples include the benzyloxy, α-phenylethoxy, β-phenylethoxy, 3-phenylpropoxy, 4-phenylbutoxy, diphenylmethoxy, 1-naphthylmethoxy and 2-naphthylmethoxy groups, of which the benzyloxy group is preferred.

Where $R^3$, $R^4$, $R^5$ or $R^6$ represents an arylalkenyl group having from 8 to 12 carbon atoms, the aryl and alkenyl parts of this group may be as defined and exemplified above for the respective component parts. Specific examples of such groups are the styryl and cinnamyl groups.

Where $R^3$, $R^4$, $R^5$ or $R^6$ represents a cycloalkyl group having from 3 to 8 carbon atoms, this may be, for example, the cyclopropyl, cyclobutyl, cyclopentyl, cyclohexyl, cycloheptyl or cyclooctyl group.

Where $R^3$, $R^4$, $R^5$ or $R^6$ represents a carboxyalkoxy group, this may be any of fee alkoxy groups having from 1 to 6 carbon atoms described above which is substituted by a carboxy group. Preferred examples include the carboxymethoxy, 2-carboxyethoxy and 4-carboxybutoxy groups, of which the carboxymethoxy group is preferred.

Where $R^3$, $R^4$, $R^5$ or $R^6$ represents an alkoxycarbonyl group, this has from 1 to 6-carbon atoms in the alkoxy part, and thus a total of from 2 to 7 carbon atoms. It may be a straight or branched chain group, and examples of such groups include the methoxycarbonyl, ethoxycarbonyl, propoxycarbonyl, isopropoxycarbonyl, butoxycarbonyl, isobutoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups, but preferably the methoxycarbonyl, ethoxycarbonyl and t-butoxycarbonyl groups, and most preferably the methoxycarbonyl or ethoxycarbonyl group.

Where $R^3$, $R^4$, $R^5$ or $R^6$ represents an aryloxycarbonyl group having from 7 to 13 carbon atoms, the aryl part of this may be any of the aryl groups defined and exemplified above. Specific examples of such groups include the phenoxycarbonyl and naphthyloxycarbonyl groups.

Where $R^3$, $R^4$, $R^5$ or $R^6$ represents an alkylcarbonyloxy group having from 2 to 7 carbon atoms, this may be any of the alkoxycarbonyl groups defined and exemplified above bonded to an oxygen atom.

Where $R^3$, $R^4$, $R^5$ or $R^6$ represents an alkanesulphonyl group, this has from 1 to 6 carbon atoms and is a straight or branched chain group. Examples of such groups include the methanesulphonyl, ethanesulphonyl, propanesulphonyl, isopropanesulphonyl, butanesulphonyl, isobutanesulphonyl, t-butanesulphonyl, pentanesulphonyl and hexanesulphonyl groups, of which the methanesulphonyl group is preferred.

Where $R^3$, $R^4$, $R^5$ or $R^6$ represents an arenesulphonyl group, the aryl part may be as defined and exemplified above, and examples include the benzenesulphonyl and n-toluenesulphonyl groups.

Where $R^3$, $R^4$, $R^5$ or $R^6$ represents an alkanoyl group having from 1 to 6 carbon atoms, and preferably from 1 to 4 carbon atoms, this may be a straight or branched-chain group, and examples include the formyl, acetyl, propionyl, butyryl, isobutyryl, pivaloyl, valeryl, isovaleryl, and hexanoyl groups, of which the acetyl group is most preferred.

Where $R^3$, $R^4$, $R^5$ or $R^6$ represents an arylcarbonyl group, the aryl part has from 6 to 10, more preferably 6 or 10, and most preferably 6, ring carbon atoms and is a carbocyclic group, which is unsubstituted or has from 1 to 5, preferably from 1 to 3 substituents, as defined and exemplified above. The preferred groups are the benzoyl and naphthoyl groups.

We particularly prefer those compounds of formula (I) in which $R^3$, $R^4 R^5$ and $R^6$ are individually the same or different and each represents a hydrogen atom, an alkyl group having from 1 to 10 carbon atoms, an alkoxy group having from 1 to 10 carbon atoms, a halogen atom, or a cycloalkyl group having from 3 to 8 carbon atoms. More preferred compounds are those in which either two or three of $R^3$, $R^4$, $R^5$ and $R^6$ represent hydrogen atoms, and still more preferably those in which one or two of $R^3$, $R^4$, $R^5$ and $R^6$ represents an ethyl or isopropyl group, or those in which three or four of $R^3$, $R^4$, $R^5$ and $R^6$ represent hydrogen atoms. The most preferred compounds are those in which one or two of $R^3$, $R^4$, $R^5$ and $R^6$ represent ethyl groups or in which one of $R^3$, $R^4$, $R^5$ and $R^6$ represents an isopropyl group and the others represent hydrogen atoms.

Where $R^8$, $R^9$, $R^{10}$ or $R^{11}$ represents an alkyl group, this may be a straight or branched chain alkyl group having from 1 to 4 carbon atoms, and examples include the methyl, ethyl, propyl, isopropyl, butyl, isobutyl and t-butyl groups, of which the methyl group is preferred.

Where $R^8$, $R^9$, $R^{10}$ or $R^{11}$ represents a phenyl group, this may be unsubstituted or it may be substituted with one or more substituents selected from the group consisting of $C_1$-$C_4$ alkyl and $C_1$-$C_4$ alkoxy groups. The alkyl and alkoxy substituents may be any of the alkyl groups exemplified above in relation to $R^8$, $R^9$, $R^{10}$ or $R^{11}$ above or any of the alkoxy groups having from 1 to 4 carbon atoms selected from the alkoxy groups exemplified in relation to $R^3$, $R^4$, $R^5$ or $R^6$ above. Examples of such groups include the phenyl group, the o-, m- or p-tolyl group, the o-, m- or p-methoxyphenyl group, the o-, m- or p-ethoxyphenyl group, the o-, m- or p-propoxyphenyl group, the o-, m- or p-butoxyphenyl group, the o-, m- or p- t-butoxyphenyl group, the 2,4,6-trimethylphenyl group and the 2,4,6-trimethoxyphenyl group. Of these, the unsubstituted phenyl group is preferred.

In one preferred embodiment of the present invention, p is 0, $R^{10}$ is a phenyl group, and $R^{11}$ is a hydrogen atom. In this embodiment, we particularly prefer that the group of formula —O—$(CHR^{12})_n$— should be attached to the benzene ring on which is a substituent in the para position to $R^{10}$, and the sulphur atom of the three membered fused ring system should be in the para position to $R^{10}$.

We prefer those compounds of formula (I) in which two, three or four of $R^8$, $R^9$, $R^{10}$ and $R^{11}$ represent hydrogen atoms, and especially those in which all of $R^8$, $R^9$, $R^{10}$ and $R^{11}$ represent hydrogen atoms.

When $R^9$ and $R^{11}$ together with the benzene rings to which they are attached, form a fused ring system, this may be, for example, a biphenylene, fluorene or phenanthrene system, preferably fluorene.

$R^7$ may be a direct bond (so that the two groups joined by $R^7$ together form biphenylyl group), an oxygen atom (so that the two groups joined by $R^7$ together form a phenoxyphenyl group), or a methylene group (so that the two groups joined by $R^7$ together form a benzylphenyl group).

n is a number from 1 to 12, more preferably from 1 to 6, and most preferably 1.

We particularly prefer compounds in which $R^{12}$ represents a hydrogen atom, and especially compounds in which $R^{12}$ represents a hydrogen atom and n is 1. Alternatively, we prefer compounds in which n is a number from 2 to 6 and one group $R^{12}$ represents a hydrogen atom, or a methyl or ethyl group and the other or others of $R^{12}$ represent hydrogen atoms.

In the compounds of the present invention, we prefer that A should represent a group of formula —$[O(CHR^{13}CHR^{14})_a]_y$— where a is an integer from 1 to 2, and y is as defined above, preferably a number from 3 to 10, more preferably a group of formula —$[OCH_2CH_2]_y$—, —$[OCH_2CH_2CH_2CH_2]_y$— or $[OCH(CH_3)CH_2]_y$—, where y is as defined above, preferably a number from 3 to 10, or a group of formula —$[O(CH_2)_bCO]_y$— or —$[O(CH_2)_bCO]_y$— or —$[O(CH_2)_bCO]_{(y-1)}$—$[O(CHR^{13}CHR^{14})_a]$—, where b is a number from 4 to 5 and y is as defined above, preferably a number from 3 to 10. Still more preferably, y is a number from 3 to 6.

In general, in the compounds of the present invention, y is preferably a number from 3 to 10, more preferably from 3 to 6. We also prefer compounds of formula (I) in which x is 2 and y is a number from 1 to 10.

It is a feature of the present invention that the compounds are of a generally polymeric nature. The polymeric nature may be provided by either the group represented by Q or the group represented by A or by both.

The polymeric polyhydroxy residue of formula Q—(A—)$^x$, which forms the core of the compounds of the present invention has a major influence on the behaviour of the compounds. In accordance with the present invention, it is important mat it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula Q—(A—)$_x$, should not have too high a molecular weight, and prefer mat the residue of formula Q—(A—)$_x$ should have a molecular weight no greater than 2000, preferably no greater than 1200, still more preferably no greater than 1000, and most preferably no greater than 800.

We particularly prefer that Q should be a residue of ethylene glycol, propylene glycol, butylene glycol, glycerol, trimethylolpropane, di-trimethylolpropane, pentaerythritol or dipentaerythritol.

It will be appreciated that, when the compounds of the present invention are analysed, the numbers a, b and y in the above formulae need not be integral, and, indeed, it is unlikely mat they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

$X^-$ represents an anion. In general, there is no particular limitation on the nature of the anion to be used. However, where the compounds of the present invention are to be used as photoinitiators, the anion should be non-nucleophilic, or essentially non-nucleophilic, as is well known in the art. It should also be relatively bulky. If the compounds are not to be used as photoinitiators, the anion need not meet these requirements. For example, in some cases, it may be desirable not to store the compound in the form of the salt which is ultimately to be used. In that case, it may be preferable to form another salt, and men convert the compound to the desired salt at or close to the point of use. In such a case, it is not necessary that the anion should be non-nucleophilic.

Examples of non-nucleophilic anions are well known to those skilled in the art, and include anions of formula $MZ_s^-$ where M represents a phosphorus, boron, antimony, arsenic, chlorine or carbon atom, Z represents a halogen atom except where M represents a halogen atom, an oxygen atom or a sulphite group, and s is an integer dependent upon the valence of M and Z. Preferred examples of such groups include the $PF_6^-$, $SbF_6^-$, $AsF_6^-$, $BF_4^-$, $B(C_6F_5)_4^-$, $R^bB(Ph)_3^-$ (where $R^b$ represents an alkyl group having from 1 to 6 carbon atoms and Ph represents a phenyl group), $R^cSO_3^-$ (where $R^c$ represents an alkyl or haloalkyl group having from 1 to 6 carbon atoms or an aryl group), $ClO_4^-$ and $ArSO_3^-$ (where Ar represents an aryl group) groups, of which the $PF_6^-$, $SbF_6^-$, $AsF_6^-$, $CF_3SO_3^-$ and $BF_4^-$ groups are preferred and the $PF_6^-$ group is most preferred.

Where the compounds of the present invention contain a carboxy group, i.e. where $R^3$, $R^4$, $R^5$ or $R^6$ represents a carboxy or carboxyalkoxy group, the resulting compounds may form esters, and these esters also form a part of the present invention. There is no particular limitation on the nature of the ester, other than those constraints well known to those skilled in the art, and preferred examples of esters include the alkyl esters, particularly those having from 1 to 12 carbon atoms, such as those containing the $C_1$-$C_{12}$ alkyl groups, and those derived from a polyalkylene glycol ether ester (especially the $C_1$-$C_4$ alkyl ethers), such as esters containing groups of formula:

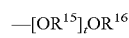
—$[OR^{15}]_tOR^{16}$ where $R^{15}$ represents an alkylene group having torn 1 to 8 carbon atoms, $R^{16}$ represents an alkyl group having from 1 to 4 carbon atoms, and t is a number from 2 to 20, preferably from 5 to 10. More preferred are groups of formula:

—$[OCH_2CHR^{17}]_tOR^{16}$ where $R^{16}$ and t are as defined above and $R^{17}$ represents an alkyl group having from 1 to 4 carbon atoms.

Any combination of the preferred substituent groups and atoms listed above in respect of $R^1$, $R^3$, $R^4$, $R^5$, $R^6$, $R^8$, $R^9$, $R^{10}$, $R^{11}$, $R^{12}$, is also envisaged by the present invention.

Particularly preferred compounds of the present invention having an especially good combination of good cure and good solubility in coating compositions are those compounds of formula (I) in which:

$R^3$, $R^4$, $R^5$ and $R^6$ are individually the same or different and each represents a hydrogen atom or an alkyl group having from 1 to 4 carbon atoms;

$R^7$ represents a direct bond;

$R^8$, $R^9$, $R^{10}$ and $R^{11}$ represent hydrogen atoms, and especially such compounds where p is 0; and A represents a group of formula —[OCH$_2$CH$_2$CH$_2$CH$_2$]$_y$—; and Q represents a residue of butylene glycol.

A further preferred class of compounds of the present invention are those compounds of formula (I) in which:

$R^3$, $R^4$, $R^5$ and $R^6$ are individually the same or different and each represents a hydrogen atom or an alkyl group having from 1 to 4 carbon atoms;

$R^7$ represents a direct bond;

$R^8$, $R^9$, and $R^{11}$ represent hydrogen atoms;

$R^{10}$ represents a phenyl group;

p is 0;

A represents a group of formula —[OCH$_2$CH$_2$CH$_2$CH$_2$]$_y$—; and

Q represents a residue of butylene glycol.

The compounds of the present invention may be prepared by reactions well known for the preparation of compounds of this type, the exact reaction route chosen depending upon the nature of the compound which it is desired to prepare.

The compounds of the present invention may be prepared by reacting a sulphoxide corresponding to ring system (IV), i.e. a compound of formula (II), with the compound corresponding to the remainder of the molecule of the desired compound, i.e. a compound of formula (III), in the presence of an acid, as shown in the following scheme:

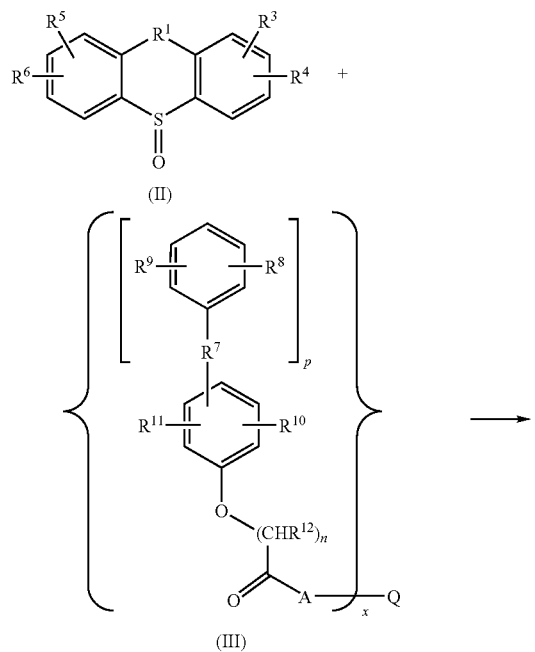

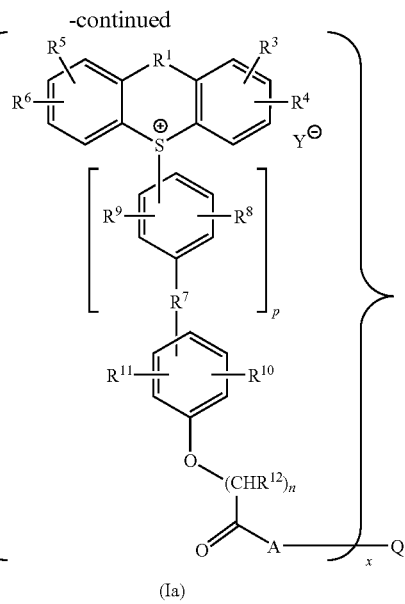

In the above formulae, $R^1$, $R^3$, $R^4$, $R^5$, $R^6$, $R^7$, $R^8$, $R^9$, $R^{10}$, $R^{11}$, $R^{12}$, A, Q, n, p and x are as defined above, and Y$^-$ represents an anion, for example a hydroxy group, which will normally be derived from the reaction. Where any one or more of $R^8$, $R^9$, $R^{10}$, or $R^{11}$ represents a hydroxy group, this is preferably protected, since it otherwise may react with the acid used in the reaction. The nature of the protecting group used is not critical to the invention, and any protecting group known in the art for use in compounds of this type may equally be used here, for example an ester group. Examples of suitable protecting groups are described in "Protective Groups in Organic Synthesis" by T. W. Greene and P. G. M. Wuts, Second Edition, 1991, published by John Wiley & Sons, Inc.

The reaction is normally and preferably effected in a solvent, the nature of which is not critical, provided that it has no adverse effect on the reagents or on the reaction and provided that it can dissolve the reagents, at least to some extent. A suitable solvent is acetic acid.

The reaction is also preferably effected in the presence of acetic anhydride and more preferably in the presence of a strong acid. Preferred is a combination of concentrated sulphuric acid and acetic anhydride.

A suitable reaction temperature is preferably below 15° C.

The sulphoxide of formula (II) and the polymeric compound of formula (III) may be prepared by well known methods.

Using the reaction scheme above, it is possible to obtain yields in excess of 90% in each reaction step, which assists the economics of the process.

In general, the anion Y$^-$ will not be the anion X$^-$ which it is desired to incorporate in fee final product. If so, then the desired anion may be introduced by an anion exchange reaction, as is well known in the field of synthetic chemistry.

Where a protected hydroxy group represented by $R^8$, $R^9$, $R^{10}$, or $R^{11}$ is present, the protecting group may, if desired, be removed by methods well known to those skilled in the art, as described in "Protective Groups in Organic Synthesis" above.

The compounds of the invention may then be separated from the reaction mixture by well known techniques and, if desired, further purified.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, and the cationic photoinitiator of the present invention, but may also include other components well known to those skilled in the art, for example, reactive diluents and, in the case of printing inks, a pigment.

A wide variety of monomers and prepolymers may be subjected to cationic photoinitiation using the compounds of the present invention as photoinitiators, and the nature of the monomers and prepolymers is not critical to the present invention. Such monomers and prepolymers typically contain cationically polymerisable groups, and general examples of such compounds include the epoxides, oxetanes, other cyclic ethers, vinyl compounds (such as vinyl and propenyl ethers, styrene and its derivatives and unsaturated polyesters), unsaturated hydrocarbons, lactones and, in the case of hybrid systems, acrylates and methacrylates.

Typical epoxides which may be used include the cycloaliphatic epoxides (such as those sold under the designations UVR6110 by Union Carbide or UVACURE 1500 by UCB), which are well known to those skilled in the art.

Other epoxy-functional oligomers/monomers which may be used include the glycidyl ethers of polyols [bisphenol A, alkyl diols or poly(alkylene oxides), which be di, tri-, tetra- or hexa-functional]. Also, epoxides derived by the epoxidation of unsaturated materials may also be used (e.g. epoxidised soybean oil, epoxidised polybutadiene or epoxidised alkenes). Naturally occurring epoxides may also be used, including the crop oil collected from *Vernonia galamensis*.

As well as epoxides, other reactive monomers/oligomers which may be used include the vinyl ethers of polyols [such as triethylene glycol divinyl ether, 1,4-cyclohexane dimethanol divinyl ether and the vinyl ethers of poly(alkylene oxides)]. Examples of vinyl ether functional prepolymers include the urethane-based products supplied by Allied Signal. Similarly, monomers/oligomers containing propenyl ether groups may be used in place of the corresponding compounds referred to above containing vinyl ether groups.

Similarly, compounds bearing oxetane groups may be used in place of the corresponding compounds referred to above containing epoxide groups. A typical oxetane is that derived from trimethylolpropane (3-ethyl-3-hydroxymethyloxetane).

Other reactive species can include styrene derivatives and cyclic esters (such as lactones and their derivatives).

It is also common to include polyols in ultraviolet cationic curable formulations, which promote the cross-linking by a chain-transfer process. Examples of polyols include the ethoxylated/propoxylated derivatives of, for example, trimethylolpropane, pentaerythritol, di-trimethylolpropane, di-pentaerythritol and sorbitan esters, as well as more conventional polyethylene oxide)s and poly(propylene oxide)s. Other polyols well known to those skilled in the art are the polycaprolactone diols, triols and tetraols, such as those supplied by Union Carbide.

Additives which may be used in conjunction with the principal components of the coating formulations of the present invention include stabilisers, plasticisers, pigments, waxes, slip aids, levelling aids, adhesion promoters, surfactants and fillers. Also, compounds which act as sensitisers for the photoinitiator, such as thioxanthone (and derivatives), benzophenone (and derivatives), hydroxyalkylphenones, anthracene (and derivatives), perylene, xanthone, pyrene and anthraquinone, may be included.

The compounds of the present invention may be included as photoinitiators in coating formulations such are well known in the art, and the precise composition of such formulations will vary depending upon the other components and the intended use, as is well known. However, a typical formulation for an ink coatable by flexography might be:

| | |
|---|---|
| Pigment | 8-20% |
| Photoinitiator | 2-6% |
| Monomer/prepolymer/oligomer | 30-90% |
| Polyol | 0-30% |
| Additives | 0-10% |

In order to enhance the solubility of the compounds of the present invention in the curable composition, they may first be dissolved in a suitable solvent, for example propylene carbonate.

The invention is further illustrated by the following non-limiting Examples.

EXAMPLE 1

Preparation of 2-isopropylthioxanthone sulphoxide

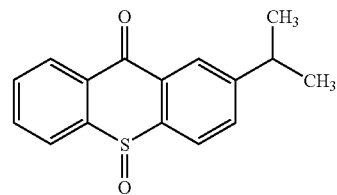

10.0 g (0.03937 moles) of 2-isopropylthioxanthone were dissolved in 630 ml of a mixture of acetonitrile and water (75% acetonitrile, 25% water by volume). Gentle heating was required to dissolve the 2-isopropylthioxanthone (35° C.). The temperature was then allowed to return to room temperature. 86.336 g of Ceric ammonium nitrate (0.15748 moles) were added in one batch. The reaction was followed by TLC (thin layer chromatography). The reaction mixture was stirred for 2.5 hours at room temperature, 400 ml of water was then added and the mixture was extracted with 1000 ml of diethyl ether. The ether layers were combined and dried with magnesium sulphate, and the ether was removed on a rotary evaporator to yield the product. At this stage the product still contained some inorganic residue. The product was therefore re-dissolved in diethyl ether, washed with water and dried with magnesium sulphate. The ether was then removed on a rotary evaporator to yield the product.

Product yield 5.54 g (52.3%) of a yellow solid.

The product was analysed by HPLC, LC-MS and IR.

IR: 1074 cm$^{-1}$ and 1032 cm$^{-1}$ S=O due to sulphoxide.

MS: M/Z 271 (Mw of cation).

HPLC: one very strong peak due to product, with a change in retention time and a shift in the characteristic chromophore compared to the starting material.

EXAMPLE 2

Preparation of Dibenzothiophene Sulphoxide

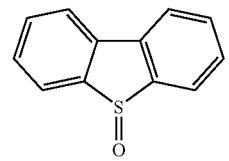

Dibenzothiophene (5.0 g, 0.027 mol) was added to acetic acid (20 ml), stirred and heated to 110° C.-120° C. until completely dissolved. An excess of peracetic acid (4.4 g, 0.0058 mol) was then added dropwise and the reaction mixture was continuously stirred at this temperature for four hours. The reaction was followed using TLC as an indication of dibenzothiophene consumption. After cooling, the reaction mixture was poured into water (40 ml), the resulting brown precipitate filtered off, washed with water and a small quantity of toluene (2-3 ml) before being dried in a vacuum oven at 50° C.; for 4 hours.

Product yield 5.0 g (92%) of brown crystals.

The product was analysed by IR, HPLC and LC-MS.

IR: 1066 cm$^{-1}$ and 1024 cm$^{-1}$ S=O due to sulphoxide.

MS: M/Z 201 (Mw of cation).

HPLC: one very strong peak due to product, with a change in retention time and a shift in the characteristic chromophore compared to the starting material.

EXAMPLE 3

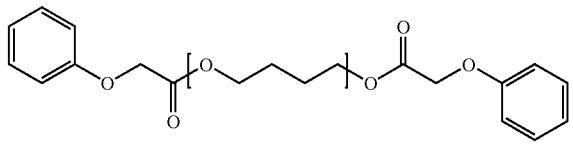

Phenoxyacetic acid (33.44 g, 0.22 mols), polytetrahydrofuran (250 molecular weight, 25 g, 0.1 mols), 0.5 g p-toluenesulphonic acid, 0.1 g butylated hydroxytoluene and 200 ml toluene were azeotropically refluxed for 2.25 hours. The solution was washed with 2×75 ml 10% aqueous potassium carbonate solution and 100 ml deionised water before azeotroping to dryness, filtering and removing all solvent on a rotary evaporator.

Yield=52.2 g slightly yellow low viscosity liquid

The product was analysed by IR.

IR: 1757-1735 cm$^{-1}$ C=O (strong) due to ester. No OH peak present.

EXAMPLE 4

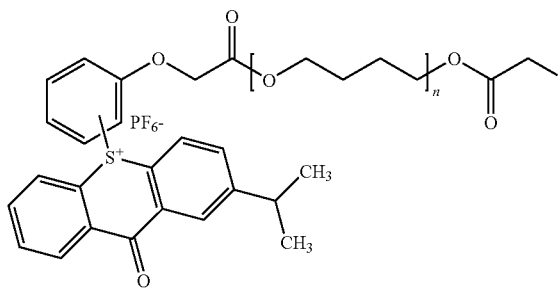

5 g of the product from Example 3 (0.00996 moles), 5.38 g of the product from Example 1 (0.0199 moles), acetic acid (18.6 ml), acetic anhydride (18.6 ml) and dichloromethane (4.7 ml) were mixed in a round-bottomed flask. The temperature of the mixture was reduced to <15° C. using a water/ice bath. Concentrated sulphuric acid (6.9 ml) was then added drop-wise, making sure the temperature did not exceed 15° C. After addition was complete, the mixture was stirred for two hours, allowing the temperature to increase to room temperature. 100 ml of water was then added and the solution was extracted with 2×100 ml dichloromethane. The dichloromethane was men removed on a rotary evaporator to yield 23.75 g of intermediate product. This was dissolved in a minimum of acetic acid and poured into a KPF$_6$ solution (5.6 g in 180 ml water). This appeared to yield a viscous liquid which was extracted with dichloromethane and washed with 3×100 ml water before drying over magnesium sulphate and removing all solvent on a rotary evaporator.

Product yield 11.86 g (91.7%) of a brown liquid.

Product analysed by IR.

IR: 845 cm$^{-1}$ (strong) due to P—F salt of product.

The position of each thioxanthone system on the associated benzene ring could not be determined exactly by analysis.

EXAMPLE 5

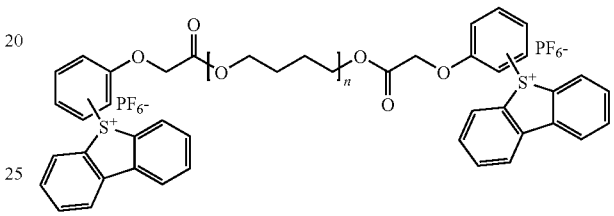

0.94 g of the product from Example 3 (0.00187 moles), 0.75 g of the product from Example 2 (0.00375 moles), acetic acid (3.5 ml), acetic anhydride (3.5 ml) and dichloromethane (0.9 ml) were mixed in a round-bottomed flask. The temperature of the mixture was reduced to <15° C. using a water/ice bath. Concentrated sulphuric acid (1.3 ml) was then added drop-wise, making sure the temperature did not exceed 15° C. After addition was complete, the mixture was stirred for two hours, allowing the temperature to increase to room temperature. 60 ml of water was then added and the solution was extracted with 2×50 ml dichloromethane. The dichloromethane was men removed on a rotary evaporator to yield 2.87 g of intermediate product. This was dissolved in a minimum of acetic acid and poured into a KPF$_6$ solution (2.0 g in 60 ml water). This appeared to yield a viscous liquid which was extracted with dichloromethane and washed with 3×100 ml water before drying over magnesium sulphate and removing all solvent on a rotary evaporator.

Product yield 2.15 g (99.1%) of a brown liquid.

Product analysed by IR.

IR: 843 cm$^{-1}$ (strong) due to P—F salt of product

The position of each dibenzothiophene system on the associated benzene ring could not be determined exactly by analysis. .

EXAMPLE 6

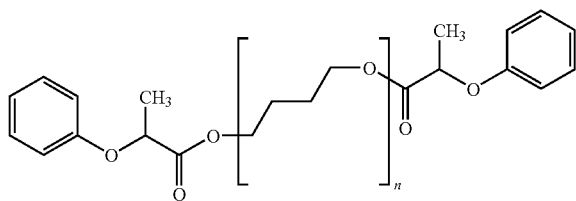

2-Phenoxypropionic acid (11.74 g, 0.07075 moles), polytetrahydrofuran (250 molecular weight, 7.69 g, 0.03076 moles), 0.16 g p-toluenesulphonic acid, 0.054 g butylated hydroxytoluene and 100 ml toluene were azeotropically refluxed for 8.75 hours. The solution was washed with 2×50 ml 10% aqueous potassium carbonate solution and 100 ml deionised water before drying over magnesium sulphate filtering and removing all solvent on a rotary evaporator.

Yield= 17.52 g slightly yellow low viscosity liquid.

The product was analysed by IR.

IR: 1755-1734 cm$^{-1}$ C=O (strong) due to ester. No OH peak present.

EXAMPLE 7

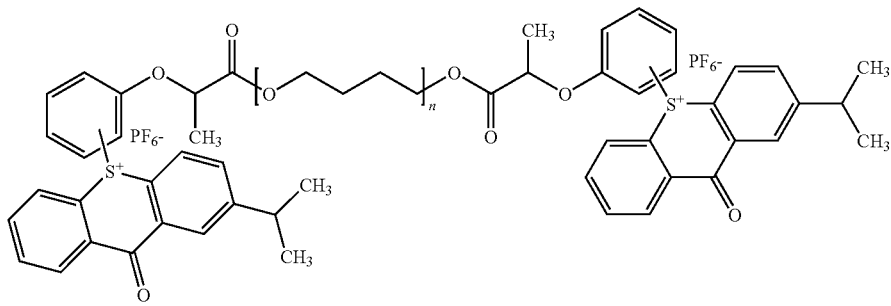

2.0 g of the product from Example 6 (0.003663 moles), 1.98 g of the product from Example 1 (0.0199 moles), acetic acid (6.8 ml), acetic anhydride (6.8 ml) and dichloromethane (1.7 ml) were mixed in a round-bottomed flask. The temperature of the mixture was reduced to <15° C. using a water/ice bath. Concentrated sulphuric acid (2.54 ml) was then added drop-wise, making sure the temperature did not exceed 15° C. After addition was complete, the mixture was stirred for two hours, allowing the temperature to increase to room temperature. 50 ml of water was then added and the solution was extracted with 2×50 ml dichloromethane. The dichloromethane was then removed on a rotary evaporator to yield 7.37 g of intermediate product. This was dissolved in a minimum of acetic acid and poured into a KPF$_6$ solution 0.4 g in 50 ml water). This appeared to yield a viscous liquid which was extracted with dichloromethane and washed with 3×100 ml water before drying over magnesium sulphate and removing all solvent on a rotary evaporator.

Product yield 4.29 g (87.3%) of a brown liquid.

Product analysed by IR.

IR: 845 cm$^{-1}$ (strong) due to P—F salt of product.

The position of each thioxanthone system on the associated benzene ring could not be determined exactly by analysis.

EXAMPLE 8

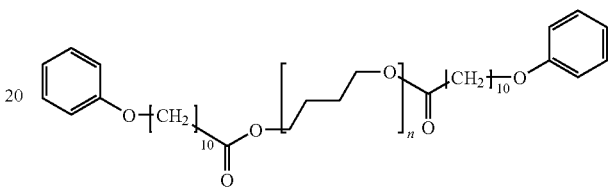

11-Phenoxyundecanoic acid (4.61 g, 0.01656 moles), polytetrahydrofuran (250 molecular weight, 1.80 g, 0.0072 moles), 0.04 g p-toluenesulphonic acid, 0.013 g butylated hydroxytoluene and 25 ml toluene were azeotropically refluxed for 9 hours. The solution was washed with 2×50 ml 10% aqueous potassium carbonate solution and 100 ml deionised water before drying over magnesium sulphate, filtering and removing all solvent on a rotary evaporator.

Yield=5.72 g slightly yellow solid.

The product was analysed by IR.

IR: 1736 cm$^{-1}$ C=O (strong) due to ester. No OH peak present.

EXAMPLE 9

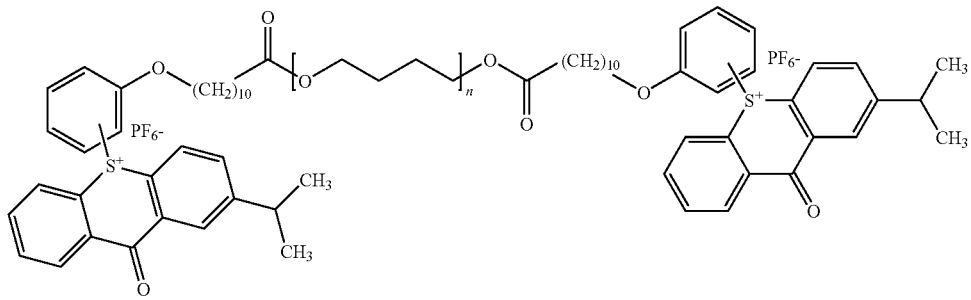

2.0 g of the product from Example 8 (0.002595 moles), 1.4 g of the product from Example 1 (0.005185 moles), acetic acid (4.8 ml), acetic anhydride (4.8 ml) and dichloromethane (1.2 ml) were mixed in a round-bottomed flask. The temperature of the mixture was reduced to <15° C. using a water/ice bath. Concentrated sulphuric acid (1.85 ml) was then added drop-wise, making sure the temperature did not exceed 15° C. After addition was complete, the mixture was stirred for two hours, allowing the temperature to increase to room temperature. 50 ml of water was then added and the solution was extracted with 2×50 ml dichloromethane. The dichloromethane was then removed on a rotary evaporator to yield 5.37 g of intermediate product. This was dissolved in a minimum of acetic acid and poured into a $KPF_6$ solution (1.4 g in 50 ml water). This appeared to yield a viscous liquid which was extracted with dichloromethane and washed with 3×100 ml water before drying over magnesium sulphate and removing all solvent on a rotary evaporator.

Product yield 2.98 g (89.95%) of a brown liquid.
Product analysed by IR.
IR: 845 $cm^-$ (strong) due to P—F salt of product.
The position of each thioxanthone system on the associated benzene ring could not be determined exactly by analysis.

EXAMPLE 10

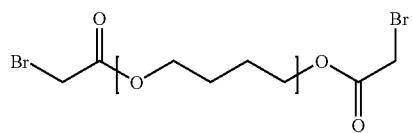

Polytetrahydrofuran (250 molecular weight, 18.75 g, 0.075 mols), bromoacetic acid (22.9 g, 0.165 mols), 0.375 g p-toluenesulphonic acid, 0.075 g butylated hydroxytoluene and 150 ml toluene were azeotropically refluxed for 5 hours. The solution was washed with 2×100 ml 10% aqueous potassium carbonate solution and 2×100 ml deionised water before azeotroping to dryness, filtering and removing all solvent on a rotary evaporator.

Yield=36.3 g colourless low viscosity liquid.

The product was analysed by IR.
IR: 1736 $cm^{-1}$ C=O (strong) due to ester. No OH peak present.

EXAMPLE 11

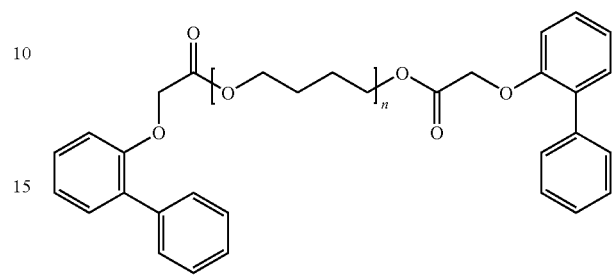

5.0 g of 2-hydroxybiphenyl (0.0294 moles), 5.08 g potassium carbonate powder (0.03676 moles) and 70 ml of methyl ethyl ketone were heated to reflux for 3 hours. The mixture was then cooled to room temperature and 7.23 g of the product from Example 10 (0.0147 moles) were added. The mixture was then heated to reflux for a total 14 hours. The mixture was then cooled to room temperature. 50 ml of toluene was added and the solution was washed with 2×100 ml 10% aqueous potassium carbonate solution and 2×100 ml deionised water before drying over magnesium sulphate. The solvent was then removed on a rotary evaporator.

Yield= 9.01 g of a slightly yellow liquid.
The product was analysed by IR.
IR: 1736 $cm^-$ C=O due to ester, 1080 $cm^{-1}$ and 1190 $cm^{-1}$ due to alkyl-aryl ether.

EXAMPLE 12

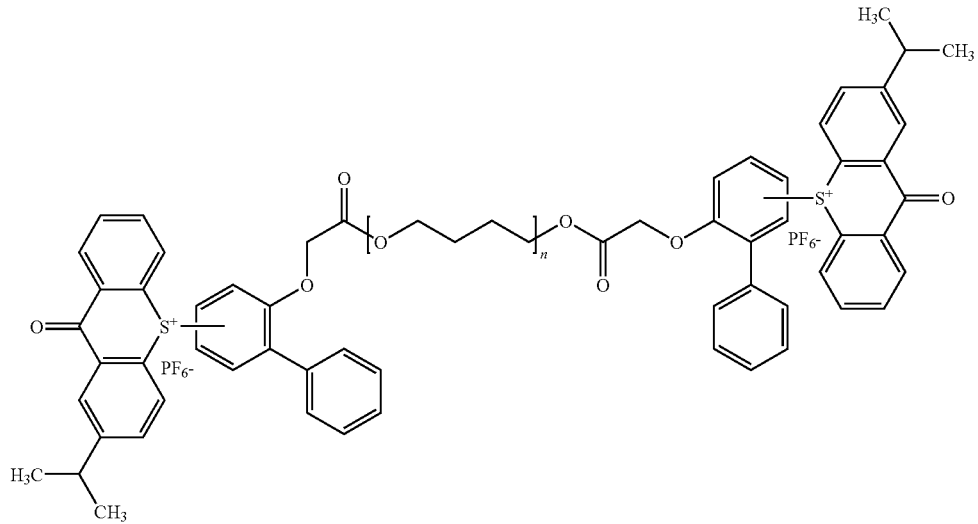

4.0 g of the product from Example 11 (0.00597 moles), 3.224 g of the product from Example 1 (0.01194 moles), acetic acid (11.1 ml), acetic anhydride (11.1 ml) and dichloromethane (2.8 ml) were mixed in a round-bottomed flask. The temperature of the mixture was reduced to <15° C. using a water/ice bath. Concentrated sulphuric acid (4.14 ml) was then added drop-wise, making sure the temperature did not exceed 15° C. After addition was complete, the mixture was stirred for two hours, allowing the temperature to increase to room temperature. 50 ml of water was then added and the solution was extracted with 2×50 ml dichloromethane. The dichloromethane was then removed on a rotary evaporator to yield 17.63 g of intermediate product. This was dissolved in a minimum of acetic acid and poured into a $KPF_6$ solution (5.0 g in 160 ml water). This appeared to yield a pasty dark green solid which was filtered, washed with water and men dried in a vacuum oven at 40° C.

Product yield 6.24 g (71.3%) of a dark green slightly sticky solid.

Product analysed by IR.

IR: 842 $cm^{-1}$ (strong) due to P—F salt of product.

It could not be determined by analysis to which of the benzene rings of the associated biphenyl system each thioxanthone system was attached nor could the position of attachment on that ring be determined.

EXAMPLE 13

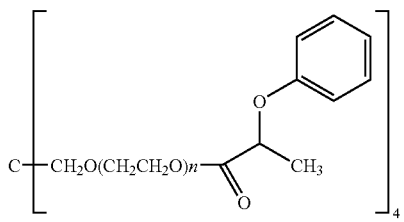

2-Phenoxypropionic acid (13.28 g, 0.07999 moles), ethoxylated pentaerythritol (EO/OH 10/4) (10.0 g, 0.0173913 moles), 0.181 g p-toluenesulphonic acid, 0.061 butylated hydroxytoluene and 100 ml toluene were azeotropically refluxed for 13 hours. The solution was washed with 2×50 ml 10% aqueous potassium carbonate solution and 100 ml deionised water before drying over magnesium sulphate, filtering and removing all solvent on a rotary evaporator.

Yield= 19.56 g clear, slightly yellow low viscosity liquid.

The product was analysed by IR.

IR: 1751-1733 $cm^{-1}$ C=O (strong) due to ester. No OH peak present.

EXAMPLE 14

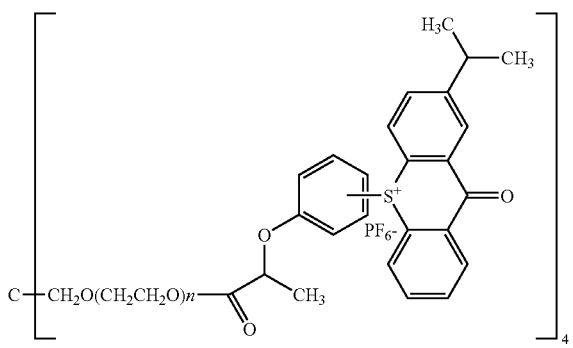

5.0 g of the product from Example 13 (0.0045289 moles), 3.47 g of the product from Example 1 (0.0128416 moles), acetic acid (16 ml), acetic anhydride (16 ml) and dichloromethane (4 ml) were mixed in a round-bottomed flask. The temperature of the mixture was reduced to <15° C. using a water/ice bath. Concentrated sulphuric acid (5.94 ml) was then added drop-wise, making sure the temperature did not exceed 15° C. After addition was complete, the mixture was stirred for two hours, allowing the temperature to increase to room temperature. 50 ml of water was then added and the solution was extracted with 2×75 ml dichloromethane. The dichloromethane was then removed on a rotary evaporator to yield 20.78 g of intermediate product. This was dissolved in a minimum of acetic acid and poured into a $KPF_6$ solution (6 g in 195 ml water). A precipitate formed that was removed by filtration and washed with water and men dried in the vacuum oven to constant weight.

Product yield 7.93 g (76.1%) of a brown solid.

Product analysed by IR.

IR: 842 $cm^{-1}$ (strong) due to P—F salt of product.

The position of each thioxanthone system on the associated benzene ring could not be determined exactly by analysis.

EXAMPLE 15

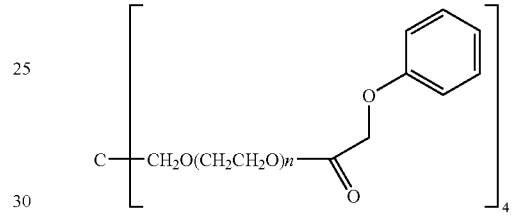

2-Phenoxyacetic acid (12.16 g, 0.07999 moles), ethoxylated pentaerythritol (EO/OH 10/4) (10.0 g, 0.017393 moles), 0.181 g p-toluenesulphonic acid, 0.061 g butylated hydroxytoluene and 100 ml toluene were azeotropically refluxed for 16½ hours. The solution was washed with 2×50 ml 10% aqueous potassium carbonate solution and 100 ml deionised water before drying over magnesium sulphate filtering and removing all solvent on a rotary evaporator.

Yield= 15.21 g clear, slightly yellow low viscosity liquid.

The product was analysed by IR.

IR: 1759 $cm^{-1}$ C=O (strong) due to ester. No OH peak present.

EXAMPLE 16

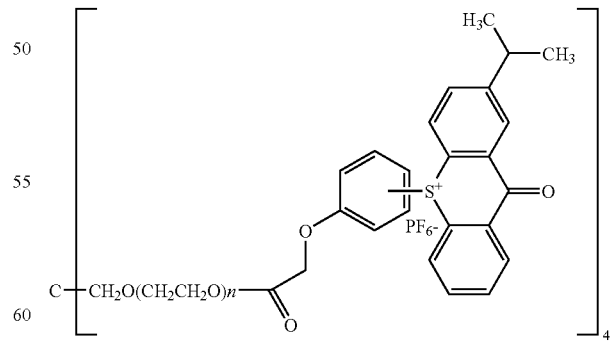

5.0 g of the product from Example 15 (0.0045004 moles), 4.86 g of the product from Example 1 (0.018 moles), acetic anhydride (14.72 g) were mixed in a round-bottomed flask. The temperature of the mixture was reduced to <10° C. using a water/ice bath. Concentrated sulphuric acid <5.64 g) was then added drop-wise, making sure the temperature did not exceed 20° C. The contents of the flask were then added to a mixture of 28.71 g methanol, 24.33 g water and 3.89 g potassium hexafluorophosphate, 2.5 ml of methanol were also used to wash out the reaction vessel and added to the mixture. The mixture was then stirred at 35-40° C. for 30 minutes. The mixture was then cooled to <10° C. and stirred for a further 30 minutes. Stirring was then stopped and the mixture was allowed to settle. The resulting residue was washed/decanted with 2×50 g methanol/water mixture (55:45 ratio). This removed any soluble impurities. The insoluble residue was then dried in the vacuum oven at 40° C. for 4 hours.

Product yield 9.0 g (73.98%) of a pasty brown solid.
Product analysed by IR.
IR; 841 cm$^{-1}$ (strong) due to P—F salt of product.
The position of each thioxanthone system on the associated benzene ring could not be determined exactly by analysis.

EXAMPLE 17

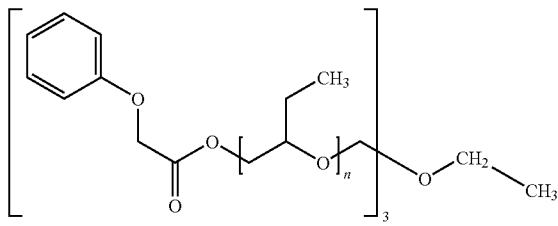

2-Phenoxyacetic acid (25.46 g, 0.1675 moles), butoxylated trimethylol propane (BuO/OH 7/4) (31.9 g, 0.05 moles), 0.5 g p-toluenesulphonic acid, 0.1 g butylated hydroxytoluene and 200 ml toluene were azeotropically refluxed for 15 hours. The solution was washed with 2×100 ml 10% aqueous potassium carbonate solution and 100 ml deionised water before drying over magnesium sulphate, filtering and removing all solvent on a rotary evaporator.

Yield=35.7 g clear, slightly straw coloured liquid.
The product was analysed by IR.
IR: 1760-1737 cm$^{-1}$ C=O (strong) due to ester. No OH peak present.

EXAMPLE 18

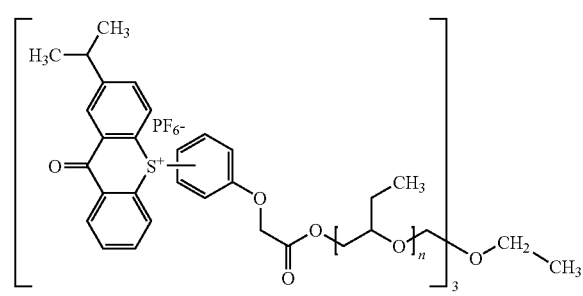

10.0 g of the product from Example 17 (0.0096153 moles), 7.79 g of the product from Example 1 (0.0288459 moles), acetic anhydride (23.6 g) were mixed in a round-bottomed flask. The temperature of the mixture was reduced to <10° C. using a water/ice bath. Concentrated sulphuric acid (9.04 g) was then added drop-wise, making sure the temperature did not exceed 20° C. The contents of the flask were then added to a mixture of 46 g methanol, 38.99 g water and 6.24 g potassium hexafluorophosphate. 2.5 ml of methanol were also used to wash out the reaction vessel and added to the mixture. The mixture was then stirred at 35-40° C. for 30 minutes. The mixture was then cooled to <10° C. and stirred for a further 30 minutes. Stirring was men stopped and the mixture was allowed to settle. The resulting residue was washed/decanted with 3× methanol/water mixture (46 g/39 g). This removed any soluble impurities. The insoluble residue was then dried in the vacuum oven at 40° C. for 4 hours.

Product yield 6.53 g (30.40%) of a pasty brown solid.
Product analysed by IR, HPLC and GPC.
IR: 841 cm$^{-1}$ (strong) due to P—F salt of product.
The position of each thioxanthone system on the associated benzene ring could not be determined exactly by analysis.

EXAMPLE 19

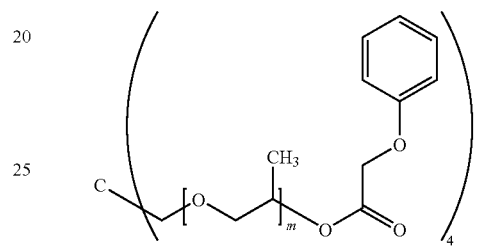

2-Phenoxyacetic acid (34.2 g, 0.225 moles), propoxylated pentaerythritol (PO/OH 17/8) (31.45 g, 0.05 moles), 0.5 g p-toluene sulphonic acid, 0.1 g butylated hydroxytoluene and 200 ml toluene were azeotropically refluxed for 15 hours. The solution was washed with 2×100 ml 10% aqueous potassium carbonate solution and 100 ml deionised water before drying over magnesium sulphate, filtering and removing all solvent on a rotary evaporator.

Yield= 48.38 g (83.1%) clear, slightly straw coloured, low viscosity liquid.
The product was analysed by IR.
IR: 1758-1738 cm$^{-1}$ C=O due to ester. No OH peak present.

EXAMPLE 20

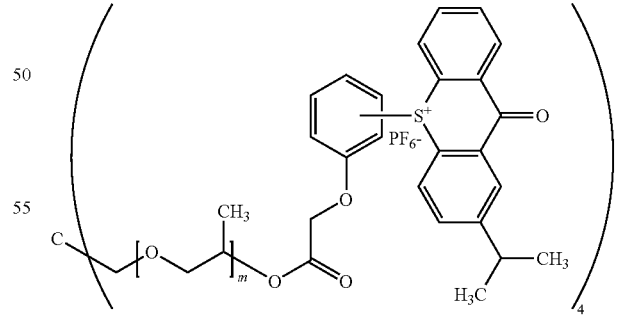

5.0 g of the product from Example 19 (0.0042918 moles), 4.635 g of the product from Example 1 (0.0171672 moles), acetic anhydride (14.05 g) were mixed in a round-bottomed flask. The temperature of the mixture was reduced to <10° C. using a water/ice bath. Concentrated, sulphuric acid (5.38 g) was then added drop-wise, making sure the temperature did not exceed 20° C. The contents of the flask were then added to a mixture of 27.38 g methanol, 23.2 g water and 3.71 g potassium hexafluorophosphate. 2.5 ml of methanol were also used to wash out the reaction vessel and added to the mixture. The mixture was then stirred at 35-40° C. for 30 minutes. The mixture was men cooled to <10° C. and stirred for a further 30 minutes. Stirring was then stopped and the mixture was allowed to settle. The resulting residue was washed/decanted with 3× methanol/water mixture (27.38 g/23.2 g). This removed any soluble impurities. The insoluble residue was then dried in the vacuum oven at 40° C. for 4 hours.

rotary evaporator to remove the organic solvent and any residual water (heating to 82° C. was required to drive off all of the solvent/water).

Product yield 41.67 g of a clear, slightly yellow liquid.

The product was analysed by IR.

IR: 1755-1737 cm$^{-1}$ C=O due to ester, 1076 cm$^{-1}$ and 1194 cm$^{-1}$ due to alkyl-aryl ether. No OH peak present.

EXAMPLE 22

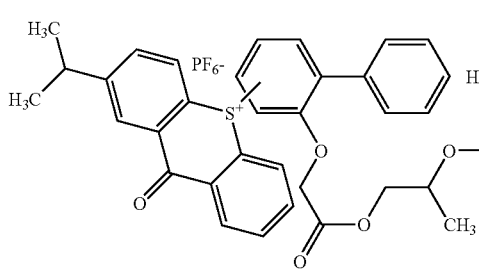
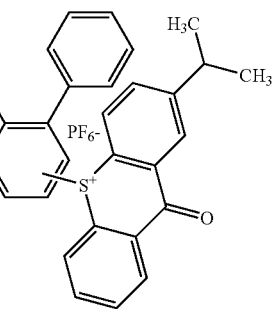

Product yield 5.47 g (46.23%) of a pasty yellow solid.

The product was analysed by IR.

IR: 841 cm$^{-1}$ (strong) due to P—F salt of product.

The position of each thioxanthone system on the associated benzene ring could not be determined exactly by analysis.

EXAMPLE 21

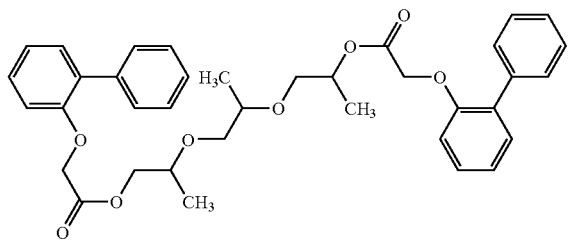

Tripropylene glycol 14.42 g (0.075 moles)s bromoacetic acid 22.92 g (0.165 moles), p-toluenesulphonic acid 0.375 g, butylated hydroxytoluene 0.075 g and toluene 50 ml were mixed in a two necked round-bottomed flask (flask 1) equipped with a temperature probe, condenser and Dean and Stark apparatus. The mixture was heated to reflux for 5 hours and then cooled to room temperature and left overnight. In a second flask (flask 2) equipped with a stirrer, condenser and temperature probe 2-hydroxybiphenyl 25.5 g (0.15 moles), potassium carbonate 25.91 g (0.1875 moles) and methyl ethyl ketone 100 ml were mixed and heated to reflux for 3 hours and men cooled to room temperature and left overnight.

The contents of flask 1 were then added to flask 2. This mixture was then heated to reflux for a further 4 hours (86-87° C.). The mixture was then cooled to <=50° C. and filtered to remove the inorganics. The inorganics were washed with a further 60 ml of methyl ethyl ketone which was then combined with the organic solution. The filter paper was pressed to maximise solvent and therefore product recovery. The organics were then washed with 2×50 ml 10% potassium carbonate solution followed by 3×50 ml water (ensuring the washings were neutral pH). The organics were men heated on 10 g of the sample from Example 21 (0.0163 moles), 2-ITX sulphoxide, 8.8 g (0.0326 moles) and acetic anhydride (20 g) were mixed in a 250 ml 3-necked round bottomed flask equipped with a stirrer, thermometer and dropping funnel.

Acetic anhydride (30 g) was added to a beaker and cooled to 10° C. Concentrated sulphuric acid (7.8 g) was added slowly controlling the temperature below 20° C. The resulting mixture was charged to the dropping runnel and added to the mixture in the flask. The addition took approximately 15 minutes and produced a black solution. This was stirred at room temperature for 20 minutes and then quenched slowly into a mixture of potassium hexafluorophosphate (6.95 g), water (90 g) and acetonitrile (23 g), controlling the quenching temperature to 10-20° C. A solid started to form during the quenching process but, as addition progressed, this turned into an oil. The product was isolated as an oil by decanting off excess water/acetonitrile. The product yield was not determined.

It could not be determined by analysis to which of the benzene rings of the associated biphenyl system each thioxanthone system was attached nor could the position of attachment on that ring be determined.

EXAMPLE 23

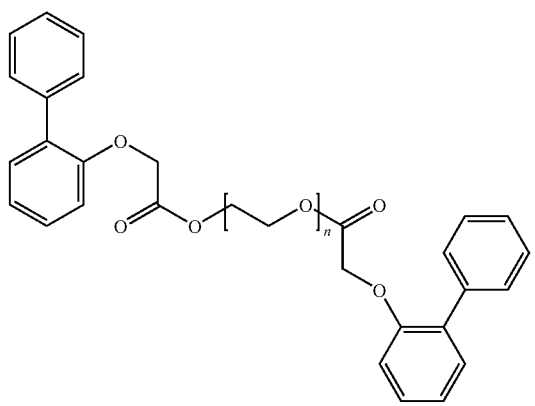

PEG200 15.00 g (0.075 moles), bromoacetic acid 22.92 g (0.165 moles), p-toluenesulphonic acid 0.375 g, butylated hydroxytoluene 0.075 g and toluene 50 ml were mixed in a two necked round-bottomed flask (flask 1) equipped with a temperature probe, condenser and Dean and Stark apparatus. The mixture was heated to reflux for 5 hours and then cooled to room temperature and left overnight. In a second flask (flask 2) equipped with a stirrer, condenser and temperature probe, 2-hydroxybiphenyl 25.5 g (0.15 moles), potassium carbonate 25.93 g (0.1875 moles) and methyl ethyl ketone 100 ml were mixed and heated to reflux for 3 hours and then cooled to room temperature and left overnight.

The contents of flask 1 were then added to flask 2. This mixture was then heated to reflux for a further 4 hours (86-87° C.). The mixture was then cooled to <= 50° C. and filtered to remove the inorganics. The inorganics were washed with a further 60 ml of methyl ethyl ketone which was then combined with the organic solution. The filter paper was pressed to maximise solvent and therefore product recovery. The organics were then washed with 2×50 ml 10% potassium carbonate solution followed by 3×50 ml water (ensuring the washings were neutral pH). The organics were then heated on a rotary evaporator to remove the organic solvent and any residual water (heating to 82° C. was required to drive off all of the solvent/water).

Product yield 19.54 g of a clear, slightly yellow liquid.

The product was analysed by BR.

IR: 1755-1737 cm$^{-1}$ C=O due to ester, 1076 cm$^{-1}$ and 1194 cm$^{-1}$ due to alkyl-aryl ether. No OH peak present.

EXAMPLE 24 into a gum. The product was isolated as a gum by decanting off excess water/acetonitrile. The product yield was not determined.

It could not be determined by analysis to which of the benzene rings of the associated biphenyl system each thioxanthone system was attached nor could the position of attachment on that ring be determined.

EXAMPLE 25

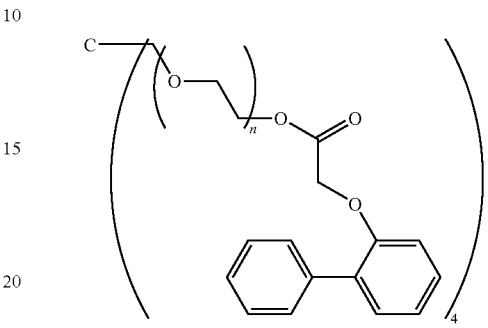

Ethoxylated pentaerythritol (3EO/4OH) 10.125 g (0.0375 moles), bromoacetic acid 22.92 g (0.165 moles), p-toluenesulphonic acid 0.375 g, butylated hydroxytoluene 0.075 g and toluene 50 ml were mixed in a two necked round-bottomed flask (flask 1) equipped with a temperature probe, condenser and Dean and Stark apparatus. The mixture was heated to

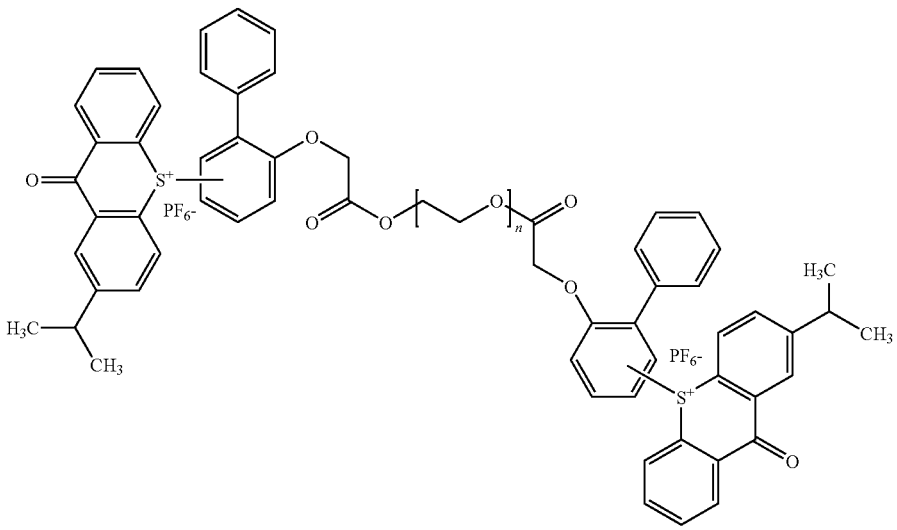

10 g of the sample from Example 23 (0.0161 moles), 2-ITX sulphoxide, 8.7 g (0.0322 moles) and acetic anhydride (20 g) were mixed in a 250 ml 3-necked round bottomed flask equipped with a stirrer, thermometer and dropping funnel.

Acetic anhydride (30 g) was added to a beaker and cooled to 10° C. Concentrated sulphuric acid (7.8 g) was added slowly controlling the temperature below 20° C. The resulting mixture was charged to the dropping funnel and added to the mixture in the flask. The addition took approximately 15 minutes and produced a black solution. This was stirred at room temperature for 20 minutes and then quenched slowly into a mixture of potassium hexafluorophosphate (6.95 g), water (90 g) and acetonitrile (23 g), controlling the quenching temperature to 10-20° C. A solid started to form during the quenching process but, as addition progressed, this turned reflux for 5 hours and then cooled to room temperature and left overnight. In a second flask (flask 2) equipped with a stirrer, condenser and temperature probe 2-hydroxybiphenyl 25.5 g (0.15 moles), potassium carbonate 25.91 g (0.1875 moles) and methyl ethyl ketone 100 ml were mixed and heated to reflux for 3 hours and then cooled to room temperature and left overnight.

The contents of flask 1 were then added to flask 2. This mixture was then heated to reflux for a further 4 hours (86-87° C.). The mixture was then cooled to <= 50° C. and filtered to remove the inorganics. The inorganics were washed with a further 60 ml of methyl ethyl ketone which was men combined with the organic solution. The filter paper was pressed to maximise solvent and therefore product recovery. The organics were then washed with 2×50 ml 10% potassium carbonate solution, followed by 3×50 ml water (ensuring the washings were neutral pH). The organics were then heated on a rotary evaporator to remove the organic solvent and any residual water (heating to 82° C. was required to drive off all of the solvent/water).

Product yield 19.54 g of a clear, slightly yellow liquid.

The product was analysed by IR.

IR: 1757-1739 cm$^{-1}$ C=O due to ester, 1076 cm$^{-1}$ and 1194 cm$^{-1}$ due to alkyl-aryl ether. No OH peak present.

EXAMPLE 26

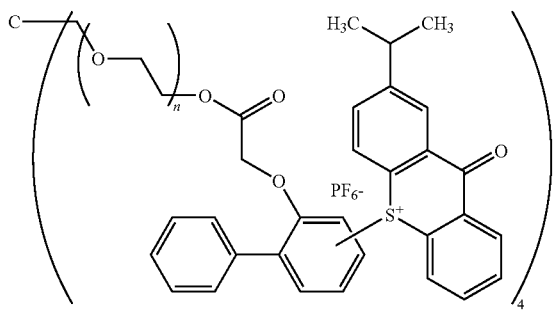

10 g of the sample from Example 25 (0.009 moles), 2-ITX sulphoxide, 9.7 g (0.0359 moles) and acetic anhydride (10 g) were mixed in a 250 ml 3-necked round bottomed flask equipped with a stirrer, thermometer and dropping funnel.

Acetic anhydride (19 g) was added to a beaker and cooled to 10° C. Concentrated sulphuric acid (8.6 g) was added slowly controlling the temperature below 20° C. The resulting mixture was charged to the dropping funnel and added to the mixture in the flask. The addition took approximately 15 minutes and produced a black solution. The solution was stirred at room temperature for 20 minutes and then quenched very slowly (over 2 hours) into a mixture of potassium hexafluorophosphate (7.6 g), water (60 g) and methanol (60 g), controlling the quenching temperature to 0-5° C. A solid started to form during the quenching process and remained as a solid throughout. The solid was filtered off and washed with deionised water (100 ml) and then dried to constant weight at 50° C.

Product yield of 22.3 g (91.8%) of a yellow solid.

The product was analysed by IR.

IR: 841 cm$^{-1}$ (strong) due to P—F salt of product.

It could not be determined by analysis to which of the benzene rings of the associated biphenyl system each thioxanthone system was attached nor could the position of attachment on that ring be determined.

EXAMPLE 27

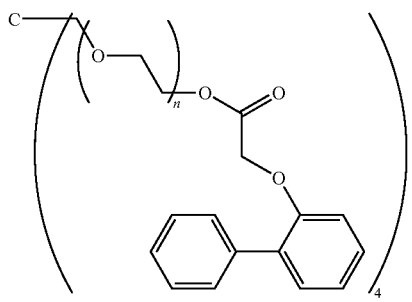

Ethoxylated pentaerythritol (10EO/4OH) 21.60 g (0.0375 moles), bromoacetic acid 22.92 g (0.165 moles), p-toluenesulphonic acid 0.375 g, butylated hydroxytoluene 0.075 g and toluene 50 ml were mixed in a two necked round-bottomed flask (flask 1) equipped with a temperature probe, condenser and Dean and Stark apparatus. The mixture was heated to reflux for 5 hours and then cooled to room temperature and left overnight. In a second flask (flask 2) equipped with a stirrer, condenser and temperature probe 2-hydroxybiphenyl 25.5 g (0.15 moles), potassium carbonate 25.91 g (0.1875 moles) and methyl ethyl ketone 100 ml were mixed and heated to reflux for 3 hours and then cooled to room temperature and left overnight.

The contents of flask 1 were then added to flask 2. This mixture was then heated to reflux for a further 4 hours (86-87° C.). The mixture was then cooled to <=50° C. and filtered to remove the inorganics. The inorganics were washed with a further 60 ml of methyl ethyl ketone which was then combined with the organic solution. The filter paper was pressed to maximise solvent and therefore product recovery. The organics were then washed with 2×50 ml 10% potassium carbonate solution, followed by 3×50 ml water (ensuring the washings were neutral pH). The organics were then heated on a rotary evaporator to remove the organic solvent and any residual water (heating to 82° C. was required to drive off all of the solvent/water).

Product yield 36.32 g of a clear, slightly yellow liquid.

The product was analysed by IR.

IR: 1757-1739 cm$^{-1}$ C=O due to ester, 1082 cm$^{-1}$ and 1194 cm$^{-1}$ due to alkyl-aryl ether. No OH peak present.

EXAMPLE 28

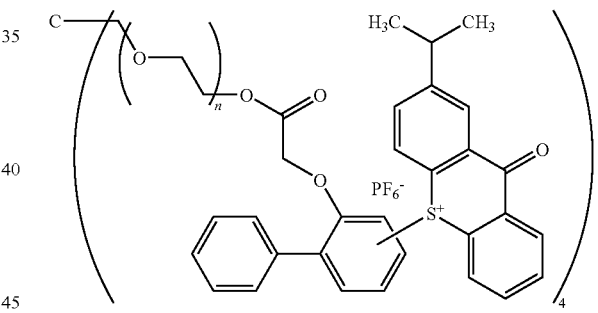

10 g of the sample from Example 27 (0.007 moles), 2-ITX sulphoxide, 7.6 g (0.028 moles) and acetic anhydride (24 g) were mixed in a 250 ml 3-necked round bottomed flask equipped with a stirrer, thermometer and dropping funnel.

Acetic anhydride (19 g) was added to a beaker and cooled to 10° C. Concentrated sulphuric acid (6.8 g) was added slowly controlling the temperature below 20° C. The resulting mixture was charged to the dropping runnel and added to the mixture in the flask. The addition took approximately 15 minutes and produced a black solution. The solution was stirred at room temperature for 20 minutes and then quenched slowly into a mixture of potassium hexafluorophosphate (6 g), water (39 g) and acetonitrile (7 g), controlling the quenching temperature to 10-20° C. A solid started to form during the quenching process but then started to form a paste. The paste was isolated by decanting off the excess solvent. Product yield was not determined.

It could not be determined by analysis to which of the benzene rings of the associated biphenyl system each thioxanthone system was attached nor could the position of attachment on that ring be determined.

EXAMPLE 29

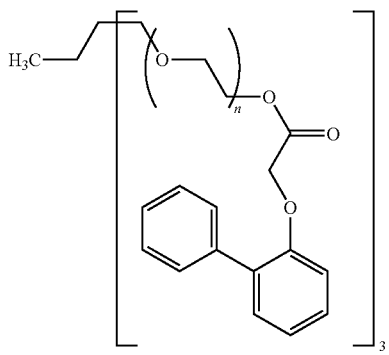

Ethoxylated trimethylolpropane (7EO/3OH) 22.20 g (0.05 moles), bromoacetic acid 22.92 g (0.165 moles), p-toluenesulphonic acid 0.375 g, butylated hydroxytoluene-0.075 g and toluene 50 ml were mixed in a two necked round-bottomed flask (flask 1) equipped with a temperature probe, condenser and Dean and Stark apparatus. The mixture was heated to reflux for 5 hours and then cooled to room temperature and left overnight. In a second flask (flask 2) equipped with a stirrer, condenser and temperature probe 2-hydroxybiphenyl 25.5 g (0.15 moles), potassium carbonate 25.91 g (0.1875 moles) and methyl ethyl ketone 100 ml were mixed and heated to reflux for 3 hours and then cooled to room temperature and left overnight.

The contents of flask 1 were then added to flask 2. This mixture was men heated to reflux for a further 4 hours (86-87° C.). The mixture was then cooled to <−50° C. and filtered to remove the inorganics. The inorganics were washed with a further 60 ml of methyl ethyl ketone which was then combined with the organic solution. The filter paper was pressed to maximise solvent and therefore product recovery. The organics were then washed with 2×50 ml 10% potassium carbonate solution, followed by 3×50 ml water (ensuring the washings were neutral pH). The organics were then heated on a rotary evaporator to remove the organic solvent and any residual water (heating to 82° C. was required to drive off all of the solvent/water).

Product yield 40.88 g of a clear, slightly yellow liquid.

The product was analysed by IR.

IR: 1757-1737 cm$^{-1}$ C=O due to ester, 1080 cm$^{-1}$ and 1194 cm$^{-1}$ due to alkyl-aryl ether. No OH peak present.

EXAMPLE 30

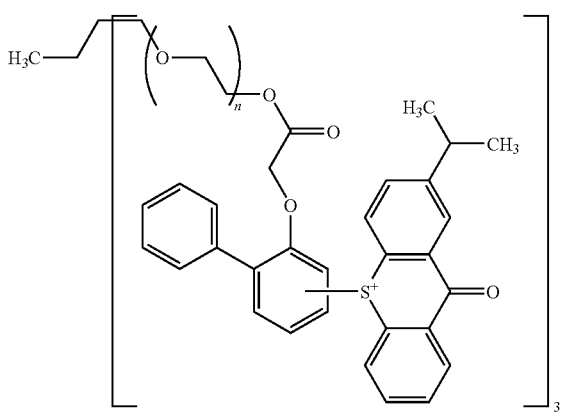

10 g of the sample from Example 29 (0.00928 moles), 2-ITX sulphoxide, 7.6 g (0.028 moles) and acetic anhydride (20 g) were mixed in a 250 ml 3-necked round bottomed flask equipped with a stirrer, thermometer and dropping funnel.

Acetic anhydride (23 g) was added to a beaker and cooled to 10° C. Concentrated sulphuric acid (6.8 g) was added slowly controlling the temperature below 20° C. The resulting mixture was charged to the dropping funnel and added to the mixture in the flask. The addition took approximately 15 minutes and produced a black solution. The solution was stirred at room temperature for 20 minutes and then quenched slowly into a mixture of potassium hexafluorophosphate (6 g), water (39 g) and acetonitrile (7 g), controlling the quenching temperature to 10-20° C. A solid started to form during the quenching process but then started to form a paste. The paste was isolated by decanting off the excess solvent. The product yield was not determined.

It could not be determined by analysis to which of the benzene rings of the associated biphenyl system each thioxanthone system was attached nor could the position of attachment on that ring be determined.

EXAMPLE 31

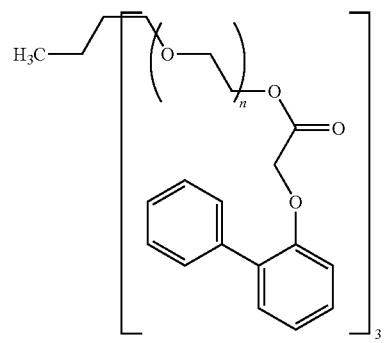

Ethoxylated trimethylolpropane (3EO/3OH) 11.30 g (0.05 moles), bromoacetic acid 22.92 g (0.165 moles), p-toluenesulphonic acid 0.375 g, butylated hydroxytoluene 0.075 g and toluene 50 ml were mixed in a two necked round-bottomed flask (flask 1) equipped with a temperature probe, condenser and Dean and Stark apparatus. The mixture was heated to reflux for 5 hours and then cooled to room temperature and left overnight. In a second flask (flask 2) equipped with a stirrer, condenser and temperature probe 2-hydroxybiphenyl 25.5 g (0.15 moles), potassium carbonate 25.91 g (0.1875 moles) and methyl ethyl ketone 100 ml were mixed and heated to reflux for 3 hours and then cooled to room temperature and left overnight.

The contents of flask 1 were then added to flask 2. This mixture was then heated to reflux for a further 4 hours (86-87° C.). The mixture was then cooled to <= 50° C. and filtered to remove the inorganics. The inorganics were washed with a further 60 ml of methyl ethyl ketone which was then combined with the organic solution. The filter paper was pressed to maximise solvent and therefore product recovery. The organics were then washed with 2×50 ml 10% potassium carbonate solution, followed by 3×50 ml water (ensuring the washings were neutral pH). The organics were then heated on a rotary evaporator to remove the organic solvent and any residual water (heating to 82° C. was required to drive off all of the solvent/water).

Product yield 32.11 g of a clear, slightly yellow liquid.

The product was analysed by IR

IR: 1757-1738 cm$^{-1}$ C=O due to ester, 1076 cm$^{-1}$ and 1194 cm$^{-1}$ due to alkyl-aryl ether. No OH peak present. .

EXAMPLE 32

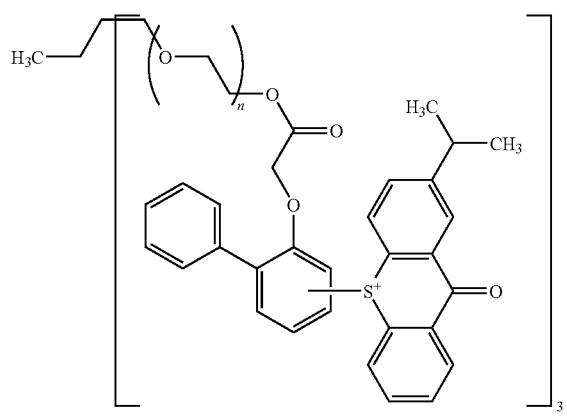

10 g of the sample from Example 31 (0.01164 moles), 2-ITX sulphoxide, 9.4 g (0.0349 moles) and acetic anhydride (20 g) were mixed in a 250 ml 3-necked round bottomed flask equipped with a stirrer, thermometer and dropping funnel.

Acetic anhydride (33 g) was added to a beaker and cooled to 10° C. Concentrated sulphuric acid (8.4 g) was added slowly controlling the temperature below 20° C. The resulting mixture was charged to the dropping funnel and added to the mixture in the flask. The addition took approximately 15 minutes and produced a black solution. The solution was stirred at room temperature for 20 minutes and men quenched slowly into a mixture of potassium hexafluorophosphate (7.4 g), water (47 g) and acetonitrile (8.6 g), controlling the quenching temperature to 10-20° C. An oil formed which was isolated by decanting off the excess solvent mixture. The product yield was not determined.

It could not be determined by analysis to which of the benzene rings of the associated biphenyl system each thioxanthone system was attached nor could the position of attachment on mat ring be determined.

EXAMPLE 33

Preparation of Thianthrene Sulphoxide

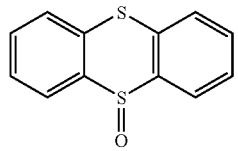

Thianthrene (5.0 g, 0.023 mol) was added to acetic acid (40 ml), stirred and heated to 110° C.-120° C. until completely dissolved. An excess of peracetic acid (4.4 g, 0.058 mol) was then added dropwise and the reaction mixture continuously stirred at this temperature for four hours. The reaction was followed using thin layer chromatography (TLC) using hexane:diethyl ether (80:20 by volume) as an indication of thianthrene consumption because thianthrene and the sulphoxide have very distinct and separate spots/rf values. After cooling, the reaction mixture was poured into water (80 ml), the resulting white precipitate filtered off, washed with water and dried in a vacuum oven at 50° C. for 4 hours.

Product yield 4.8 g (90%) of white crystals.

The product was analysed by IR, LCMS and HPLC.

IR: 1078 cm$^{-1}$ and 1029 cm$^{-1}$ S=O due to sulphoxide.

MS: M/Z 233 (Mw of cation).

HPLC: one very strong peak due to product, with a change in retention time and a shift in the characteristic chromophore compared to the starting material.

EXAMPLE 34

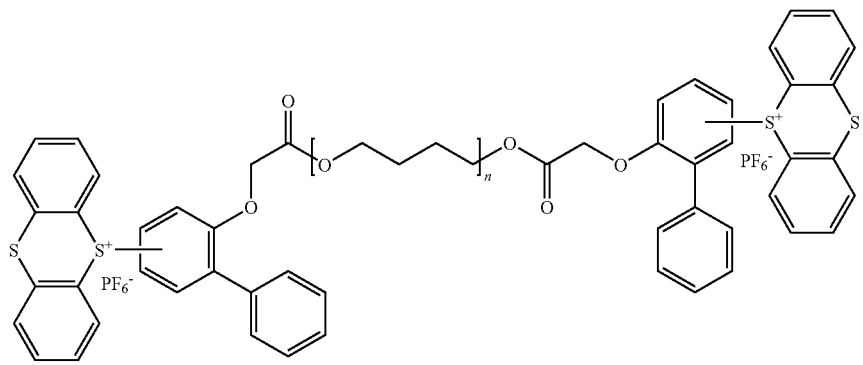

In a two-necked round bottomed flask (flask 1) equipped with a stirrer, condenser and temperature probe were added 5.36 g (0.0525382 moles) acetic anhydride. The temperature was reduced to ~10° C. and 4.675 g (0.046455 moles) concentrated sulphuric acid was added dropwise, ensuring the temperature did not exceed 20° C.

In a second flask (flask 2) the following were mixed:— 3.463 g thianthrene sulphoxide (0.0149252 moles, from Example 33), di(biphenyl-2-oxy)polytetrahydrofuran (5.0 g, 0.0074626 moles, from Example 11), acetic anhydride (6.85 g). The flask was equipped with a stirrer, thermometer and a condenser. The temperature of the mixture was reduced to <10° C. using a water/ice bath. The contents from flask 1 were then added to the contents of flask 2, ensuring the temperature was maintained <20° C. throughout. 2 g of acetic anhydride were used to wash out flask 1 to ensure all of the mixture was added to flask 2. The mixture was then stirred for 30 minutes. The contents of the flask were then added to 23.8 g methanol/ 20.2 g water/3.23 g potassium hexafluorophosphate. (2 ml of methanol were used to ensure all of the contents from the flask were washed into methanol/water/KPF6 salt mixture). The mixture was stirred for 30 minutes at approx. 40° C. The temperature was then reduced to approximately 10° C. and the mixture stirred for a further 30 minutes. The soluble materials were then decanted off and the pasty material was washed/decanted with a further 3× methanol/water (25.8 g/20.2 g). The resulting pasty solid was then dried in a vacuum oven at 40° C. for >4 hours. The solid product was then ground up using a mortar and pestle.

Product yield 7.14 g (68.84%) of a slightly yellow/brown solid.

The product was analysed by IR.

IR: 839 cm$^{-1}$ (strong) due to P—F salt of product.

It could not be determined by analysis to which of the benzene rings of the associated biphenyl system each thianthrene system was attached nor could the position of attachment on that ring be determined.

EXAMPLE 35

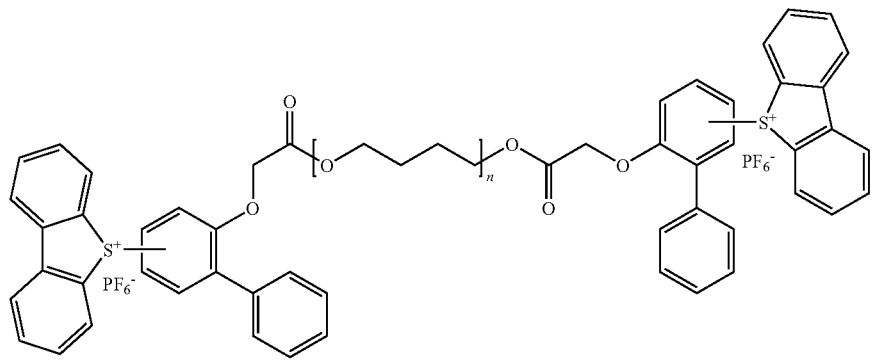

In a two-necked round bottomed flask (flask 1) equipped with a stirrer, condenser and temperature probe add 5.36 g (0.0525382 moles) acetic anhydride. The temperature was reduced to ~10° C. and 4.675 g (0.046455 moles) concentrated sulphuric acid was added dropwise, ensuring the temperature did not exceed 20° C.

In a second flask (flask 2) the following were mixed:—2.985 g dibenzothiophene sulphoxide (0.0149252 moles, from example 2), di(biphenyl-2-oxy)polytetrahydrofuran (5.0 g, 0.0074626 moles, from Example 11), acetic anhydride (6.85 g). The flask was equipped with a stirrer, thermometer and a condenser. The temperature of the mixture was reduced to <10° C. using a water/ice bath. The contents from flask 1 were then added to the contents of the second flask ensuring the temperature was maintained <20° C. throughout. 2 g of acetic anhydride were used to wash out flask 1 to ensure all of the mixture was added to flask 2. The mixture was then stirred for 30 minutes. The contents of the flask were then added to 23.8 g methanol/20.2 g water/3.23 g potassium hexafluorophosphate. (2 ml of methanol were used to ensure all of the contents from the flask were washed into methanol/water/KPF6 salt mixture). The mixture was stirred for 30 minutes at approx. 40° C. The temperature was then reduced to approximately. 10° C. and the mixture stirred for a further 30 minutes. The soluble materials were then decanted off and the pasty material was washed/decanted with a further 3× methanol/water (25.8 g/20.2 g). The resulting pasty solid was then dried in a vacuum oven at 40° C. for >4 hours. The solid product was then ground up using a mortar and pestle.

Product yield 4.57 g (46.2%) of a brown solid.

The product was analysed by IR.

IR: 841 cm$^{-1}$ (strong) due to P—F salt of product.

It could not be determined by analysis to which of the benzene rings of the associated biphenyl system each dibenzothiophene system was attached nor could the position of attachment on that ring be determined.

EXAMPLE 36

Varnish Formulations

The following varnish formulations were used in the evaluation experiments with all photoinitiators used at 4% active photoinitiator in the formulation.

| Material Code/Description | Standard Varnish 1 | Standard Varnish 2 | Experimental Varnish |
|---|---|---|---|
| Uvacure 1500 | 91.8 | 94.5 | 95.8 |
| Tegorad 2100 | 0.2 | 0.2 | 0.2 |
| Uvacure 1592 | 8.0 | — | — |
| Irgacure 250 | — | 5.3 | — |
| Experimental Photoinitiator | — | — | 4.0 |
| Total | 100.0 | 100.0 | 100.0 |

Uvacure 1500 is a cycloaliphatic epoxide monomer from UCB

Tegorad 2100 is a wetting aid from TEGO

Uvacure 1592 is a standard triarylsulphonium salt photoinitiator from UCB (supplied as a 50% solution in propylene carbonate.)

Irgacure 250 is a standard diaryliodonium salt photoinitiator from CIBA (supplied as a 75% solution in propylene carbonate.)

The experimental photoinitiators used were those produced in Examples 4, 5, 7, 9, 12, 14, 16, 18, 20, 26, 34 and 35.

Summary of Caring Experiments.

The varnishes were printed onto Leneta opacity charts using a No. 0 K-bar and draw down pad. The prints were passed at 80 m/min through a Primarc "Maxicure" UV curing rig using a single 300 W/inch medium pressure mercury arc lamp operating on its half power setting. The number of passes to achieve full cure was noted, along with the print colour and odour.

All the experimental photoinitiators had acceptable cure performance against the 2 commercial standard photoinitiators, with those containing the initiators of Examples 4, 12 and 26 having cure at least as fast as the best standard Uvacure 1592. All the experimental photoinitiators were soluble in fee test formulation and gave no odour on cure. The slight yellowing observed with the experimental photoinitiators can be addressed by formulation techniques known to those skilled in the art. The yellowing would not be an issue in pigmented inks containing the experimental photoinitiators. The results are shown in the following Table.

Summary of Curing Experiments.

The inks were printed onto a white OPP substrate (Propafilm RB30 ex UCB) using an "Easiproof" hand held flexo proofer with anilox tool 41. The prints were passed through a Primarc Maxicure UV curing rig fitted with a 300 Watts/inch medium pressure mercury arc lamp at several different line speeds and lamp power settings. The number of passes to achieve complete cure was determined using the "thumb-twist" test.

| | | | Curing Results Summary | | |
|---|---|---|---|---|---|
| Initiator Code | Initiator Description | Soluble | Number of passes to cure Experimental varnish formulation | Odour | Colour of film |
| Uvacure 1592 | standard triarylsulphonium salt photoinitiator | No | 1 | Strong | Colourless |
| Irgacure 250 | standard diaryliodonium salt photoinitiator | Yes | 3 | Very strong | Colourless |
| Example 4 | PolyTHF250 Di(phenoxy acetic)ester/2x2-ITX | Yes | 1 | No | Slightly Yellow |
| Example 5 | PolyTHF250 Di(phenoxy acetic)ester/2xDBTP | Yes | 4 | No | Slightly Yellow |
| Example 7 | PolyTHF250 Di(phenoxy propionic)ester/2x2-ITX | Yes | 2 | No | Slightly yellow |
| Example 9 | PolyTHF250 Di(phenoxy undecanoic)ester/2x2-ITX | Yes | 4 | No | Slightly yellow |
| Example 12 | PolyTHF250 Di(biphenyl-2-oxy acetic)ester/2x2-ITX | Yes | 1 | No | Slightly yellow |
| Example 14 | Ethoxylated Pentaerythritol (10EO/4OH) Tetra(phenoxy propionic)ester/4x2-ITX | Yes | 2 | No | Slightly yellow |
| Example 16 | Ethoxylated Pentaerythritol (10EO/4OH) Tetra(phenoxy acetic)ester/4x2-ITX | Yes | 2 | No | Slightly yellow |
| Example 18 | Butoxylated TMP Tri(phenoxy acetic)ester/3x2-ITX | Yes | 2 | No | Slightly yellow |
| Example 20 | Propoxylated Pentaerythritol (17PO/8OH) Tetra(phenoxy acetic)ester/4x2-ITX | Yes | 2 | No | Slightly yellow |
| Example 26 | Ethoxylated Pentaerythritol (3EO/4OH) Tetra(biphenyl-2-oxy acetic)ester/4x2-ITX | Yes | 1 | No | Slightly yellow |
| Example 34 | PolyTHF250 Di(biphenyl-2-oxy acetic)ester/2xthianthrene | Yes | 2 | No | Colourless |
| Example 35 | PolyTHF250 Di(biphenyl-2-oxy acetic)ester/ 2xdibenzothiophene | Yes | 2 | No | Slightly yellow |

EXAMPLE 37

Magenta Ink Formulations

The following magenta ink formulations were used in the evaluation experiments.

| Material Code/Description | Standard Ink | Experimental Ink |
|---|---|---|
| Pigment concentrate | 56.8 | 56.8 |
| Uvacure 1500 | 34.7 | 34.7 |
| Tegorad 2100 | 0.5 | 0.5 |
| Propylene carbonate | 4.0 | 4.0 |
| Standard Photoinitiator | 4.0 | — |
| Experimental Photoinitiator | — | 4.0 |

The standard photoinitiators used were Uvacure 1592 (triarylsulphonium salt photoinitiator from UCB, supplied as a 50% solution in propylene carbonate) and Irgacure 250<diaryliodonium salt photoinitiator from CIBA Specialty Chemicals, supplied as a 75% solution in propylene carbonate).

Uvacure 1500 is a cycloaliphatic epoxide monomer from UCB

Tegorad 2100 is a wetting aid from TEGO

| | Lamp at 50% power | | Lamp at 100% Power |
|---|---|---|---|
| Photoinitiator | No. passes to cure at 80 m/min | No. passes to cure at 100 m/min | No. passes to cure at 120 m/min |
| Uvacure 1592 | 1 | 2 | 2 |
| Irgacure 250 | — | 4 | 2 |
| Example 12 | 2-3 | 3 | 2 |

These results demonstrate that the novel photoinitiators of this invention have similar cure performance in inks to standard commercial cationic photoinitiators.

EXAMPLE 38

GC-MS Headspace Analysis from Varnishes

The following varnish formulations were used in the evaluation experiments.

| Material Code/<br>Description | Sulphonium salt<br>formulations | Iodonium salt<br>formulation |
|---|---|---|
| Uvacure 1500 | 75 | 77.5 |
| TMPO | 20.9 | 18.9 |
| Tegorad 2100 | 0.1 | 0.1 |
| Propylene carbonate | 2 | — |
| Photoinitiator | 2 | 1.5 |
| Esacure KIP 150 | — | 2 |

The standard photoinitiators used were Uvacure 1592 (triarylsulphonium salt photoinitiator from UCB, supplied as a 50% solution in propylene carbonate) and IGM 440 (diaryliodonium salt photoinitiator from IGM.

Uvacure 1500 is a cycloaliphatic epoxide monomer from UCB

Tegorad 2100 is a wetting aid from TEGO

TMPO is a monofunctional oxetane alcohol diluent from Perstorp.

Esacure KIP 150 is a hydroxyalkylphenone photoinitiator from Lamberti.

The varnishes were printed onto aluminium foil using a No. 0 K-bar and draw down pad. The prints were passed twice through a Primarc Maxicure UV curing rig fitted with a 300 Watts/inch medium pressure mercury arc lamp at 80 m/min. Under these conditions the samples were over-cured, which was desirable in order to maximise the amount of by-product formation. 200 cm2 of each sample was placed in a sealed tube and subjected to a standard headspace analysis procedure where they are heated to 200° C. for 10 minutes and then the headspace volume transferred to a gas chromatograph fitted with a mass spectrometer detector via a heated transfer line.

The compounds detected in these analyses are shown below. No attempt was made to quantify individual materials. Note that there were also several peaks common to all samples that derive from the Uvacure 1500.

| Photoinitiator | Materials detected in Head-space procedure derived from photoinitiator |
|---|---|
| Uvacure 1592 | Diphenyl sulphide<br>Several small unidentified peaks* |
| IGM 440 | Toluene<br>Iodobenzene<br>Several unidentified peaks |
| Example 4 | 2-isopropyl thioxanthone<br>unidentified phenoxy terminated material |

*Benzene would also be expected from this analysis but was not seen due to the solvent delay used in this standard GC method.

These results demonstrate that for Example 4, the photoinitiator by-products detected are the commonly used free radical photoinitiator ITX, and an unidentified phenoxy terminated material. In the case of this phenoxy by-product, its occurrence can be limited further through the use of higher functionality and/or higher molecular weight polyol stating materials. These results contrast with the undesirable materials released from the 2 standard photoinitiators.

GC-MS Headspace Analysis from Inks

The following ink formulations were used in the evaluation experiments.

GC-MS Headspace Analysis from Inks

The following ink formulations were used in the evaluation experiments,

| Material Code/<br>Description | Sulphonium salt<br>formulations | Iodonium salt<br>formulation |
|---|---|---|
| Pigment concentrate | 54 | 54 |
| Uvacure 1500 | 4.2 | 4.2 |
| TMPO | 33.3 | 32.3 |
| Tegorad 2100 | 0.5 | 0.5 |
| Propylene carbonate | 4 | 4 |
| Photoinitiator | 4 | 3 |
| Irgacure 184 | — | 2 |

The standard photoinitiators used were Uvacure 1592 (triarylsulphonium salt photoinitiator from UCB, supplied as a 50% solution in propylene carbonate) and IGM 440 (diaryliodonium salt photoinitiator from IGM.

Irgacure 184 is a hydroxyalkylphenone photoinitiator from CIBA. All other raw materials are as disclosed above.

Inks were printed onto aluminium foil using an "Easiproof" hand anilox flexo proofer and cured on a Primarc Maxicure UV rig at 100 m/min with a single 300 W/inch medium pressure mercury arc lamp operating at full power.

250 cm² of each sample was placed in a sealed tube and subjected to a standard headspace analysis procedure where they are heated to 200° C. for 10 minutes and then the headspace volume transferred to a gas chromatograph fitted with a mass spectrometer detector via a heated transfer line.

The compounds detected in these analyses are shown below. No attempt was made to quantify individual materials. Note that there were also several peaks common to all samples that derive from the Uvacure 1500.

| Photoinitiator | Materials detected in Head-space procedure derived from photoinitiator |
|---|---|
| Uvacure 1592 | Diphenyl sulphide<br>Several small unidentified peaks* |
| IGM 440 | Toluene<br>Iodobenzene<br>Several unidentified peaks |
| Example 12 | 2-isopropyl thioxanthone |

*Benzene would also be expected from this analysis but was not seen due to the solvent delay used in this standard GC method.

These results demonstrate that for Example 12, the only photoinitiator by-product detected was the commonly used free radical photoinitiator ITX. This result contrasts with the undesirable materials released from the 2 standard photoinitiators.

The invention claimed is:

1. Compounds of formula (I):

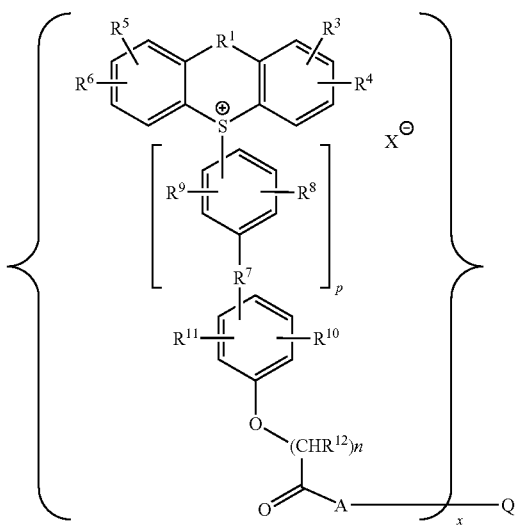

where:

R$^1$ represents a direct bond;

R$^3$, R$^4$, R$^5$ and R$^6$ are independently selected from hydrogen atoms and substituents α, defined below;

R$^8$, R$^9$, R$^{10}$ and R$^{11}$ are independently selected from hydrogen atoms, hydroxy groups, C$_1$-C$_4$ alkyl groups, and phenyl groups which are unsubstituted or substituted by at least one substituent selected from the group consisting of C$_1$-C$_4$ alkyl groups and C$_1$-C$_4$ alkoxy groups;

or R$^9$ and R$^{11}$ are joined to form a fused ring system with the benzene rings to which they are attached;

R$^7$ represents a direct bond, an oxygen atom or a —CH$_2$— group;

p is 0 or 1;

said substituents α are: a C$_1$-C$_{20}$ alkyl group, a C$_1$-C$_{20}$ alkoxy group, a C$_2$-C$_{20}$ alkenyl group, a halogen atom, a nitrile atom, a hydroxyl group, a C$_6$-C$_{10}$ aryl group, a C$_7$-C$_{13}$ aralkyl group, a C$_6$-C$_{10}$ aryloxy group, a C$_7$-C$_{13}$ aralkyloxy group, a C$_8$-C$_{12}$ arylalkenyl group, a C$_3$-C$_8$ cycloalkyl group, a carboxy group, a C$_2$-C$_7$ carboxyalkoxy group, a C$_2$-C$_7$ alkoxycarbonyl group, a C$_7$-C$_{13}$ aryloxycarbonyl group, a C$_2$-C$_7$ alkylcarbonyloxy group, a C$_1$-C$_6$ alkanesulphonyl group, a C$_6$-C$_{10}$ arenesulphonyl group, a C$_1$-C$_6$ alkanoxyl group or a C$_7$-C$_{11}$ arylcarbonyl group;

n is a number from 1 to 12;

R$^{12}$ represents a hydrogen atom, a methyl group or an ethyl group, and, when n is greater than 1, the groups or atoms represented by R$^{12}$ may the same as or different from each other;

A represents a group of formula —[O(CHR$^{13}$CHR$^{14}$)$_a$]$_y$—, —[O(CH$_2$)$_b$CO]$_y$—, or —[O(CH$_2$)$_b$CO]$_{(y-1)}$—[O(CHR$^{13}$CHR$^{14}$)$_a$]—, where:

one of R$^{13}$ and R$^{14}$ represents a hydrogen atom and the other represents a hydrogen atom, a methyl group or an ethyl group;

a is a number from 1 to 2;

b is a number from 4 to 5;

Q is selected from the group consisting of ethylene glycol, propylene glycol, butylene glycol, glycerol, trimethylolpropane, di-trimethylolpropane, pentaerythritol and dipentaerythritol;

x is a number greater than 1 but no greater than the number of available hydroxyl groups in Q;

y is a number from 1 to 10; and

X$^-$ represents an anion;

and esters thereof.

2. Compounds according to claim 1, in which x is a number greater than 1 but no greater than 2, and y is a number from ito 10; or in which x is a number greater than 2, and y is a number from 3 to 10.

3. Compounds according to claim 1, in which n is a number from 1 to 6.

4. Compounds according to claim 1, in which n is 1.

5. Compounds according to claim 1, in which R$^{12}$ represents a hydrogen atom.

6. Compounds according to claim 1, in which n is a number from 2 to 6 and one group R$^{12}$ represents a hydrogen atom, or a methyl or ethyl group and the other or others R$^{12}$ represent hydrogen atoms.

7. Compounds according to claim 1, in which y is a number from 3 to 10.

8. Compounds according to claim 1, in which A represents a group of formula —[O(CHR$^{13}$CHR$^{14}$)$_a$]$_y$, where a is an integer from 1 to 2, and y is a number from 3 to 10.

9. Compounds according to claim 1 in which A represents a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is a number from 3 to 10.

10. Compounds according to claim 1, in which A represents a group of formula —[O(CH$_2$)$_b$CO]$_y$—, where b is a number from 4 to 5 and y is a number from 3 to 10.

11. Compounds according to claim 1, in which A represents a group of formula —[O(CH$_2$)$_b$CO]$_{(y-1)}$—[O(CHR$^{13}$CHR$^{14}$)$_a$]—, where a is a number from 1 to 2, b is a number from 4 to 5 andy is a number from 3 to 10.

12. Compounds according to claim 1, in which x is 2 and y is a number from 1 to 10.

13. Compounds according to claim 1, in which y is a number from 3 to 6.

14. Compounds according to claim 1, in which the residue Q—(A—)$_x$ has a molecular weight no greater than 2000.

15. Compounds according to claim 14, in which the residue Q—(A—)$_x$ has a molecular weight no greater than 1200.

16. Compounds according to claim 15, in which the residue Q—(A—)$_x$ has a molecular weight no greater than 1000.

17. Compounds according to claim 16, in which the residue Q—(A—)$_x$ has a molecular weight no greater than 800.

18. Compounds according to claim 1, in which R$^3$, R$^4$, R$^5$ and R$^6$ are independently selected from hydrogen atoms, C$_1$-C$_{10}$ alkyl groups, C$_1$-C$_{10}$ alkoxy groups, halogen atoms, and C$_3$-C$_8$ cycloalkyl groups.

19. Compounds according to claim 1, in which three or four of R$^3$, R$^4$, R$^5$ and R$^6$ represents hydrogen atoms.

20. Compounds according to claim 18, in which one or more R$^3$, R$^4$, R$^5$ and R$^6$ represents an ethyl or isopropyl group.

21. Compounds according to claim 1, in which two, three or four of R$^8$, R$^9$, R$^{10}$ and R$^{11}$ represents hydrogen atoms.

22. Compounds according to claim 1, in which all of R$^5$, R$^9$, R$^{10}$ and R$^{11}$ represent hydrogen atoms.

23. Compounds according to claim 1, in which: R$^3$, R$^4$, R$^5$ and R$^6$ are individually the same or different and each represents a hydrogen atom or an alkyl group having 1 to 4 atoms;

$R^7$ is a direct bond;

$R^5$, $R^9$, $R^{10}$ and $R^{11}$ represent hydrogen atoms; and

A represents a group of formula —[OCH$_2$CH$_2$CH$_2$CH$_2$]$_y$—; and

Q represents a butylene glycol.

24. Compounds according to claim 1, in which $R^3$, $R^4$, $R^5$ and $R^6$ are individually the same or different and each represents a hydrogen atom or an alkyl group having from 1 to 4 carbon atoms;

$R^7$ represents a direct bond;

$R^8$, $R^9$, and $R^{11}$ represent hydrogen atoms;

$R^{10}$ represents a phenyl group;

p is 0;

A represents a group of formula —[OCH$_2$CH$_2$CH$_2$CH$_2$]$_y$—; and

Q represents butylene glycol.

25. Compounds according to claim 1, in which X$^-$ represents PF$_6^-$, SbF$_6^-$, AsF$_6^-$, BF$_4^-$, B(C$_6$F$_5$)$_4^-$, R$^a$B(Ph)$_3^-$ (where R$^a$ represents a C$_1$-C$_6$ alkyl group and Ph represents a phenyl group), R$^b$SO$_3^-$ (where R$^b$ represents a C$_1$-C$_6$ alkyl or haloalkyl group or an aryl group), ClO$_4^-$, or ArSO$_3^-$ (where Ar represents an aryl group) group.

26. Compounds according to claim 24, in which X$^-$ represents PF$_6^-$, SbF$_6^-$, AsF$_6^-$, CF$_3$SO$_3^-$ or BF$_4^-$ group.

27. Compounds according to claim 25, in which X$^-$ represents a PF$_6^-$ group.

28. Compounds according to claim 1, having the formula (Ia):

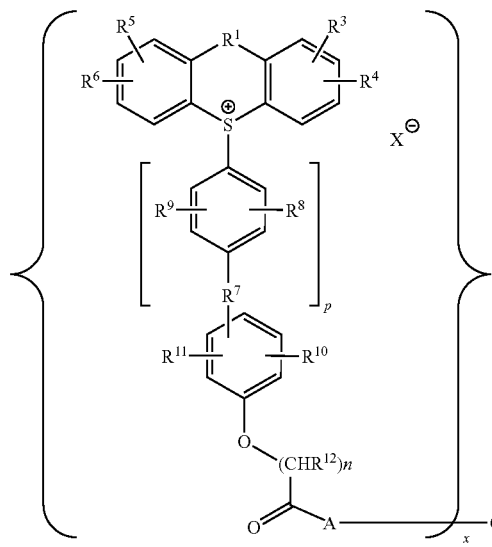

in which $R^1$, $R^3$, $R^4$, $R_5$, $R_6$, $R_7$, $R^8$, $R^9$, $R^{10}$, $R^{11}$, $R^{12}$, p, x, n, A, Y and X$^-$ are as defined in claim 1.

29. An energy-curable composition comprising (a) a polymerizable monomer, prepolymer or oligomer; and (b) a photoinitiator which is a compound of formula (I), as claimed in claim 1.

30. A process for preparing a cured polymeric composition by exposing a composition according to claim 29 to curing energy.

31. A process according to claim 30, in which the curing energy is ultraviolet radiation.

* * * * *